(12) United States Patent
Florin et al.

(10) Patent No.: US 9,340,592 B2
(45) Date of Patent: May 17, 2016

(54) CHO/CERT CELL LINES

(75) Inventors: Lore Florin, Biberach an der Riss (DE); Eric Becker, Hochdorf (DE); Hitto Kaufmann, Ulm (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 118 days.

(21) Appl. No.: 13/318,509

(22) PCT Filed: May 4, 2010

(86) PCT No.: PCT/EP2010/056009
§ 371 (c)(1),
(2), (4) Date: Jan. 13, 2012

(87) PCT Pub. No.: WO2010/128032
PCT Pub. Date: Nov. 11, 2010

(65) Prior Publication Data
US 2012/0100553 A1  Apr. 26, 2012

(30) Foreign Application Priority Data

May 5, 2009  (EP) .................................... 09159439
Jun. 4, 2009  (EP) .................................... 09161907

(51) Int. Cl.
C12N 15/85 (2006.01)
C12N 15/63 (2006.01)
A61K 31/711 (2006.01)
C12P 21/08 (2006.01)
C07K 14/47 (2006.01)

(52) U.S. Cl.
CPC ..................................... C07K 14/47 (2013.01)

(58) Field of Classification Search
CPC ........... C12N 15/67; C12N 1/00; C12N 15/85
See application file for complete search history.

(56) References Cited

U.S. PATENT DOCUMENTS

| | | | |
|---|---|---|---|
| 5,521,297 A | 5/1996 | Daggett et al. | |
| 5,869,250 A | 2/1999 | Cheng et al. | |
| 7,326,768 B2 | 2/2008 | Saus et al. | |
| 7,820,809 B2 | 10/2010 | Khvorova et al. | |
| 8,221,999 B2 | 7/2012 | Kaufmann et al. | |
| 2003/0069181 A1 | 4/2003 | Wong | |
| 2003/0190319 A1 | 10/2003 | Adolf et al. | |
| 2004/0175758 A1 | 9/2004 | Saus et al. | |
| 2005/0255487 A1 | 11/2005 | Khvorova et al. | |
| 2007/0082345 A1 | 4/2007 | Ota et al. | |
| 2008/0113351 A1 | 5/2008 | Naito et al. | |
| 2008/0300207 A1* | 12/2008 | Kaufmann et al. | 514/44 |
| 2009/0018099 A1 | 1/2009 | Kaufmann et al. | |
| 2012/0100553 A1 | 4/2012 | Florin et al. | |
| 2013/0177919 A1 | 7/2013 | Kaufmann et al. | |
| 2013/0196430 A1 | 8/2013 | Kaufmann et al. | |
| 2013/0197196 A1 | 8/2013 | Kaufmann et al. | |

FOREIGN PATENT DOCUMENTS

| | | |
|---|---|---|
| EP | 1652530 A1 | 5/2006 |
| WO | 0050607 A2 | 8/2000 |
| WO | 2007001851 A2 | 1/2007 |
| WO | 2008107388 A1 | 9/2008 |
| WO | 2010128032 A1 | 11/2010 |

OTHER PUBLICATIONS

Florin et al, Heterologous expression of the lipid transfer protein CERT increases therapeutic protein productivity of mammalian cells, J Biotechnology, 2009, pp. 84-90.*
Liljedahl, Monika et al; Protein Kinase D Regulates the Fission of Cell Surface Destined Transport Carriers from the Trans-Golgi Network; Cell (2001) vol. 104 pp. 409-420.
Litvak, Vladimir et al; Maintenance of the Diacylglycerol Level in the Golgi Apparatus by the Nir2 Protein is Critical for Golgi Secretory Function; Nature Cell Biology (2005) vol. 7 No. 3 pp. 225-234.
Loewen, Christopher J.R. et al; A Conserved ER Targeting Motif in three Families of Lipid Binding Proteins and in Opi1p Binds VAP; The EMBO Journal (2003) vol. 22 No. 9 pp. 2025-2035.
LoveJoy, Brett et al; Crystal Structure of a Synthetic Triple-Stranded ?-Helical Bundle; Science (1993) vol. 259 pp. 1288-1293.
Lunn, Charles A. et al. "Localization of Thioredoxin from *Escherichia coli* in an Osmotically Sensitive Compartment" (1982) Journal of Biological Chemistry, vol. 257, pp. 11424-11430.
Madden, Thomas L. et al; Applications of Network BLAST Server; Methods of Enzymology (1996) vol. 266 pp. 131-141. Maeda, Yusuke et al; Recruitment of Protein Kinase D to the Trans-Golgi Network via the First Cysteine-Rich Domain; The EMBO Journal (2001) vol. 20 No. 21 pp. 5982-5990.
Meunier, Jean-Claude "Nociceptin/orphanin FQ and the opioid receptor-like ORL1 receptor" (1997) European Journal of Pharmacology vol. 340, pp. 1-15.
Olayioye, Monilola A. et al; StarD10, a START Domain Protein Overexpresses in Breast Cancer, Functions as a Phospholipid Transfer Protein; The Journal of Biological Chemistry (2005) vol. 280 No. 29 pp. 27436-27442.
Overall, Christopher M. et al; Validating Matrix Metalloproteinases as Drug Targets and Anti-Targets for Cancer Therapy; Nature Reviews (2006) vol. 6 pp. 227-239.
Pack, Peter et al; Improved Bivalent Miniantibodies, with Identical Avidity as Whole Antibodies, Produced by High Cell Density Fermentation of *Escherichia coli*; Bio/Technology (1993) vol. 11 pp. 1271-1277.
Pack, Peter et al; Tetravalent Miniantibodies with High Avidity Assembling in *Escherichia coli*; Journal Molecular Biology (1995) vol. 246 pp. 28-34.

(Continued)

Primary Examiner — Maria Marvich
(74) Attorney, Agent, or Firm — Michael P. Morris; Atabak R. Royaee

(57) ABSTRACT

The invention concerns the field of cell culture technology. The invention describes production host cell lines comprising vector constructs comprising a CERT S132 A expression cassette. Those cell lines have improved growth characteristics and high CERT S132A expression levels. The invention especially concerns two cell lines deposited with the DSMZ under the number DSM ACC2989 (CHO/CERT 2.20) and DSM AC-C2990 (CHO/CERT 2.41). The invention further concerns a method of generating such preferred production host cells and a method of producing proteins using the two cell lines deposited with the DSMZ under the number DSM ACC2989 (CHO/CERT 2.20) and DSM ACC2990 (CHO/CERT 2.41).

12 Claims, 9 Drawing Sheets

(56) References Cited

OTHER PUBLICATIONS

Pak, S.C.O. et al; Super-CHO—A Cell Line Capable of Autocrine Growth under Fully Defined Protein-Free Conditions; Cytotechnology (1996) vol. 22 pp. 139-146.
Parkin, Edward et al. "Dual Mechanisms for Shedding of the Cellular Prion Protein" The Journal of Biological Chemistry (2004) vol. 279, No. 1, pp. 1170-1178.
Perisic, Olga et al; Crystal Structure of a Diabody, a Bivalent Antibody Fragment; Structure (1994) vol. 2 pp. 1217-1226.
Perry, Ryan J. et al; Molecular Mechanisms and Regulation of Ceramide Transport; Biochimica et Biophysica Acta (2005) vol. 1734 pp. 220-234.
Raya, Angel et al. "Goodpasture Antigen-binding Protein, the Kinase that Phosphorylates the Goodpasture Antigen, is an Alternatively Spliced Variant Implicated in Autoimmune Pathogenesis" The Journal of Biological Chemistry, 275 (2000) pp. 40392-40399.
Rykx, An et al; Protein Kinase D: A Family Affair; FEBS Letters (2003) vol. 546 pp. 81-86.
Schroder, Marin; The Unfolded Protein Response; Molecular Biotechnology (2006) vol. 34 pp. 279-290.
Scopes, Robert K.; Classical and Modern Techniques in Protein Purification; Protein Purification: Micro to Macro (1987) pp. 1-15 Alan R. Liss, Inc.
Seth, Gargi et al; Engineering Cells for Cell Culture Bioprocessing-Physiological Fundamentals; Adv Biochem Engin/BioTechnology (2006) vol. 101 pp. 119-164.
Shaffer, A.L. et al; XBP1, Downstream of Blimp-1, Expands the Secretory Apparatus and Other Organelles, and Increases Protein Synthesis in Plasma Cell Differentiation; Immunity (2004) vol. 21 pp. 81-93.
Soccio, Raymond E. et al; StAR-Related Lipid Transfer (START) Proteins: Mediators of intracellular Lipid Metabolism; The Journal of Biological Chemistry (2003) vol. 278 No. 25 pp. 22183-22186.
Somerharju, Pentti ; Pyrene-Labeled Lipids as Tools in Membrane Biophysics and Cell Biology; Chemistry and Physics of Lipids (2002) vol. 116 pp. 57-74.
Tigges, Marcel et al; Xbp1-Based Engineering of Secretory Capacity Enhances the Productivity of Chinese Hamster Ovary Cells; Metabolic Engineering (2006) vol. 8 pp. 264-272.
Toth, Balazs et al; Phosphatidylinositol 4-Kinase III? Regulates the Transport of Ceramide Between the Endoplasmic Reticulum and Golgi; The Journal of Biological Chemistry (2006) vol. 281 No. 47 pp. 36369-36377.
Tsujishita, Yosuke et al; Structure and Lipid Transport Mechanism of a StAR-Related Domain; Nature Structural Biology (2000) vol. 7 No. 5 pp. 408-414.
Urlaub, Gail et al; Deletion of the Diploid Dihydrofolate Reductase Locus from Cultured Mammalian Cells; Cell (1983) vol. 33 pp. 405-412.
Vega, Rick B. et al; Protein Kinases C and D Mediate Agonist-Dependent Cardiac Hypertrophy through Nuclear Export of Histone Deacetylase 5; Mollecular and Cellular Biology (2004) vol. 24 No. 19 pp. 8374-8385.
Visintin, Michela, et al. "Selection of antibodies for intracellular function using a two-hybrid in vivo system" PNAS, vol. 96, No. 21, (1999) pp. 11723-11728.
Wang, Qiming J. et al; PKD at the Crossroads of DAG and PKC Signaling; Trends and Pharmacological Sciences (2006) vol. 27 No. 6 pp. 317-323.
Wang, Ying et al; The RAS Effector RIN1 Directly Competes with RAF and is regulated by 14-3-3 Proteins; Mollecular and Cellular Biology (2002) vol. 22 No. 3 pp. 916-926.
Weigert, Roberto et al; CtBP/BARS Induces Fission of Golgi Membranes by Acylating Lysophosphatidic Acid; Nature (1999) vol. 402 pp. 429-433.
Werner, Rolf G. et al; Economic Aspects of Commercial Manufacture of Biopharmaceuticals; Journal of Biotechnology (2004) vol. 113 pp. 171-182.
Wirtz, Karel W.A. et al; Phospholipid Transfer Proteins in Perspective; FEBS Letters (2006) vol. 580 pp. 5436-5441.
Wurm, Florian M., Production of Recombinant Protein Therapeutics in Cultivated Mammalian Cells; Nature Biotechnology (2004) vol. 22 No. 11 pp. 1393-1398.
www.ncbi.nlm.nih.gov/nuccore/5031716 NCBI Reference Sequence : NM 0057131.1. Jun. 1, 2008 and Sequence Alignment Data.
Yeaman, Charles et al; Protein Kinase D Regulates Basolateral Membrane Protein Exit from Trans-Golgi Network; Nature Cell Biology (2004) vol. 6 No. 2 pp. 106-112.
Zhang, Jinghui et al; PowerBLAST: A Network Blast Application for Interactive or Automated Sequence Analysis and Annotation; Genome Research (1997) vol. 7 pp. 649-656.
Al-Rubeai, Mohamed et al; Apoptosis in Cell Culture; Current Opinion in Biotechnology (1998) vol. 9 pp. 152-156.
Alpy, Fabien et al; Give Lipids a START: The StAR-Related Lipid Transfer (START) Domain in Mammals; Journal of Cell Science (2005) vol. 118 pp. 2791-2801.
Altschul, Stephen F. et al; Basic Local Alignment Search Tool; Journal Molecular Biology (1990) vol. 215 pp. 403-410.
Anel, Alberto Marcelo Diaz et al; PKCeta is Required for Beta 1 Gamma2/Beta3Gamma2- and PKD-Mediated Transport to the Cell Surface and the Organization of the Golgi Apparatus; Journal Cell Biology (2005) vol. 169 No. 1 pp. 83-91.
Bard, Frederic et al; Functional Genomics Reveals Genes Involved in Protein Secretion and Golgi Organization; Nature (2006) vol. 439 No. 2 pp. 604-607.
Barnes, Louise M. et al; Mammalian Cell Factories for Efficient and Stable Protein Expression; Current Opinion in Biotechnology (2006) vol. 17 pp. 381-386.
Barnes, Louise M. et al; Molecular Analysis of Successful Cell Line Selection in Transfected GS-NSO Myeloma Cells; Biotechnology and Bioengineering (2007) vol. 96 No. 2 pp. 337-348.
Baron, Carole L. et al; Role on Dyacylglycerol in PKD Recruitment to the TGN and Protein Transport to the Plasma Membrane; Science (2002) vol. 295 pp. 325-328.
BLAST of SEQ ID No. 17, (2010) Retrieved from Internet: URL: http://blast.ncbi.nim.hig.gov/Blast.cgi pp. 1-5.
BLAST, SEQ ID Nos. 17 and 19. (2010) Retrieved from Internet. URL: http://blast.ncbi.nim.hig.gov/Blast.cgi pp. 1-3.
Blobel, Carl P.; Adams: Key Components in EGFR Signaling and Development; Nature Ter. Molecular Cell Biology (2005) vol. 6 pp. 32-43.
Bork, Peer "Powers and Pitfalls in Sequence Analysis: The 70% Hurdle" European Molecular Biology Laboratory, Genome Research (2000) V 10, pp. 398-400.
Borth, Nicole et al; Effect on Increased Expression of Protein Disulfide Isomerase and Heavy Chain Binding Protein on Antibody Secretion in a Recombinant CHO Cell Line; Biotechnology Prog. (2005) vol. 21 pp. 106-111.
Bowie, James U. et al. "Deciphering the Message in Protein Sequences: Tolerance to Amino Acid Substitutions" Science (1990) vol. 247, pp. 1306-1310.
Brewer, Joseph W. et al; Building an Antibody Factory: A Job for the Unfolded Protein Response; Nature Immunology (2005) vol. 6 No. 1 pp. 23-29.
Burgess, Wilson H. et al. "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue" Journal Cell Biology (1990) vol. 111, pp. 2129-2138.
Buzas, B et al. "Regulation of nociceptin/orphanin FQ gene expression by ceramide in astrocytes" Neuroscience 2002 Abstract, Nov. 4, 2002.
Chen-Kiang, Selina; Cell-Cycle Control of Plasma Cell Differentiation and Tumorigenesis; Immunological Reviews (2003) vol. 194 pp. 39-47.
Chiang, Gisela G. et al; Bcl-xl Mediated Increased Production of Humanized Monoclonal Antibodies in Chinese Hamster Ovary Cells; Biotechnology and Bioengineering (2005) vol. 91 pp. 779-792.
Davis, Raymond et al; Effect of PDI Overexpression on Recombinant Protein Secretion in CHO Cells; Biotechnology Prog. (2000) vol. 16 pp. 736-743.

(56) References Cited

OTHER PUBLICATIONS

Ding, Y. et al. "Ceramide-induced Upregulation of Redoxin Proteins in RPE and Effect of Hepatocyte Growth Factor" (2005) Investigative Ophthalmology & Visual Science vol. 46, E-Abstract 1620-B389, 2 pgs.
Doppler, Heike et al; A Phosphorylation State-Specific Antibody Recognizes Hsp27, a Novel Substrate of Protein Kinase D; The Journal of Biological Chemistry (2005) vol. 280 No. 15 pp. 15013-15019.
Dorner, Andrew J. et al; The Levels of Endoplasmic Reticulum Proteins and ATP Affect Folding and Secretion of Selective Proteins; Biologicals (1994) vol. 22 pp. 103-112.
Egeblad, Mikala et al; New Functions for the Matrix Metalloproteinases in Cancer Progression; Nature Review Cancer (2002) vol. 2 pp. 161-174.
Fugmann, Tim et al. "Regulation of secretory transport by protein kinase D-mediated phosphorylation of the cermaide transfer protein" Journal of Cell Biology (2007) vol. 178, No. 1, pp. 15-22.
Fukunaga, Takuya et al; Implications of Sphingolipid Metabolism in the Stability of the Golgi Apparatus; Journal of Cell Science (2000) vol. 113 pp. 3299-3307.
Garcia-Cardena, Guillermo et al. "Targeting of nitric oxide synthase to endothelial cell caveolae via palmitoylation: Implications for nitric oxide signaling" (1996) Proc. Natl. Acad. Sci., vol. 93, pp. 6648-6453.
Hanada, Kentaro et al. "CERT and intracellular trafficking of ceramide" Biochimica et Biophysica Acta (2007) 1771 pp. 644-653.
Hanada, Kentaro et al; Molecular Machinery for Non-Vesicular Trafficking of Ceramide; Nature (2003) vol. 426 pp. 803-809.
Hanada, Kentaro; Discovery of the Molecular Machinery CERT for Endoplasmic Reticulum-to-Golgi Trafficking of Ceramide; Molecular and Cellular Biochemistry (2006) vol. 286 pp. 23-31.
Hanahan, Douglas et al; The Hallmarks of Cancer; Cell (2000) vol. 100 pp. 57-70.
Hausser, Angelika et al; Protein Kinase D Regulates Vesicular Transport by Phosphorylating and Activating Phosphatidylinositol-4 Kinase III? at the Golgi Complex; Nature Cell Biology (2005) vol. 7 No. 9 pp. 880-886.
Hausser, Angelika, et al. Structural requirements for localization and activation of protein kinance C μ(PKC μ) at the Golgi compartment. The Rockerfeller University Press, The Journal of Cell Biology, V 156 No. 1, Jan. 7, 2002, pp. 65-74.
Hooker, Andrew D. et al; Constraints on the Transport and Glycosylation of Recombinant IFN-? in Chinese Hamster Ovary and Insect Cells; Biotechnology and Bioengineering (1999) vol. 63 pp. 559-572.
Hu, Shi-Zhen et al; Minibody: A Novel Engineered Anti-Carcinoembryonic Antigen Antibody Fragment (Single-Chain Fv-Ch3) Which exhibits Rapid, High-Level targeting of Xenografts; Cancer Research (1996) vol. 56 pp. 3055-3061.
Huston, James S. et al; Protein Engineering of Antibody Binding Sites: Recovery of Specific Activity in an Anti-Digoxin Single-Chain Fv Analogue Produced in *Escherichia Coli*; Proc. Natl. Acad. Sci. USA. (1988) vol. 85 pp. 5879-5883.
Iglesias, Teresa et al; Identification and Cloning of Kidins220, a Novel Neuronal Substrate of Protein Kinase D; The Journal of Biological Chemistry (2000) vol. 275 No. 51 pp. 40048-40056.
Iwakoshi, Neal N. et al; The X-Box Binding Protein-1 Transcription Factor is Required for Plasma Cell Differentiation and the unfolded Protein Response; Immunological Reviews (2003) vol. 194 pp. 29-38.
Jaggi, Meena et al; E-Cadherin Phosphorylation by Protein Kinase D1/Protein Kinase C? is Associated with Altered Cellular Aggregation and Motility in Prostate Cancer; Cancer Research (2005) vol. 65 No. 2 pp. 483-492.
Kaufmann, Hitto et al; Metabolic Engineering of Mammalian Cells for Higher Protein Yield; Gene Transfer and Expression in Mammalian Cells (2003) chapter 15 pp. 457-469, Elsevier Science B.V.
Kawano, Miyuki et al; Efficient trafficking of Ceramide from the Endoplasmic Reticulum to the Golgi Apparatus Requires a VAMP-Associated Protein-Interacting FFAT Motif of CERT; Journal of Biological Chemistry (2006) vol. 281 No. 40 pp. 30279-30288.
Kortt, Alexander A. et al; Single-Chain Fv Fragments of Anti-Neuraminidase Antibody NC10 Containing Five and Ten-Residue Linkers Form Dimers and with Zero-Residue Linker a Trimer; Protein Engineering (1997) vol. 10 No. 4 pp. 423-433.
Kumagai, Keigo et al. "CERT Mediates Intermembrane Transfer of Various Molecular Species of Ceramides*" Journal of Biological Chemistry (2005) vol. 280, No. 8, pp. 6488-6495.
Lazar, Eliane et al. "Transforming Growth Factor a: Mutation of Aspartic Acid 47 and Leucine 48 Results in Different Biological Activities" Molecular and Cellular Biology (1988) pp. 1247-1252.
Levine, Tim et al; Inter-Organelle Membrane Contact Sited; through a Glass, Darkly; Current Opinion in Cell Biology (2006) vol. 18 pp. 371-378.
Levine, Timothy P. et al; Targeting of Golgi-Specific Pleckstrin Homology Domains Involves Both PtdIns 4-Kinase-Dependent and -Independent Components; Current Biology (2002) vol. 12 pp. 695-704.
Li, Huige et al. "Dual Effect of Ceramide on Human Endothelial Cells Induction of Oxidative Stress and Transciptional Upregulation of Endothelial Nitric Oxide Synthase" (2002) Circulation pp. 2250-2256.

* cited by examiner (A)

(B)

(A)

(B)

(A)

(B)

(A)

SEQUENCE LISTING

<160> NUMBER OF SEQ ID NOS: 6

<210> SEQ ID NO 1
<211> LENGTH: 1919
<212> TYPE: DNA
<213> ORGANISM: Artificial
<220> FEATURE:

<223> OTHER INFORMATION: FLAG-CERT SA fusion construct

<400> SEQUENCE: 1

| | | | | | |
|---|---|---|---|---|---|
| gccagtgtgc | tggaattcac | catggcccca | ctagccgact | acaaggacga | cgatgacaag | 60 |
| atgtcggata | atcagagctg | gaactcgtcg | ggctcggagg | aggatccaga | gacggagtct | 120 |
| gggccgcctg | tggagcgctg | cggggtcctc | agtaagtgga | caaactacat | tcatgggtgg | 180 |
| caggatcgtt | gggtagtttt | gaaaaataat | gctctgagtt | actacaaatc | tgaagatgaa | 240 |
| acagagtatg | gctgcagagg | atccatctgt | cttagcaagg | ctgtcatcac | acctcacgat | 300 |
| tttgatgaat | gtcgatttga | tattagtgta | aatgatagtg | tttggtatct | tcgtgctcag | 360 |
| gatccagatc | atagacagca | atggatagat | gccattgaac | agcacaagac | tgaatctgga | 420 |
| tatggatctg | aatccagctt | gcgtcgacat | ggcgcaatgg | tgtccctggt | gtctggagca | 480 |
| agtggctact | ctgcaacatc | cacctcttca | ttcaagaaag | gccacagttt | acgtgagaag | 540 |
| ttggctgaaa | tggaaacatt | tagagacatc | ttatgtagac | aagttgacac | gctacagaag | 600 |
| tactttgatg | cctgtgctga | tgctgtctct | aaggatgaac | ttcaaaggga | taaagtggta | 660 |
| gaagatgatg | aagatgactt | tcctacaacg | cgttctgatg | gtgacttctt | gcatagtacc | 720 |
| aacggcaata | agaaaagtt | atttccacat | gtgacaccaa | aaggaattaa | tggtatagac | 780 |
| tttaaggggg | aagcgataac | ttttaaagca | actactgctg | gaatccttgc | aacactttct | 840 |
| cattgtattg | aactaatggt | taaacgtgag | acagctggc | agaagagact | ggataaggaa | 900 |
| actgagaaga | aagaagaac | agaggaagca | tataaaaatg | caatgacaga | acttaagaaa | 960 |
| aaatcccact | ttggaggacc | agattatgaa | gaaggcccta | acagtctgat | taatgaagaa | 1020 |
| gagttctttg | atgctgttga | agctgctctt | gacagacaag | ataaaataga | gaacagtca | 1080 |
| cagagtgaaa | aggtgagatt | acattggcct | acatccttgc | cctctggaga | tgccttttct | 1140 |
| tctgtgggga | cacatagatt | tgtccaaaag | gttgaagaga | tggtgcagaa | ccacatgact | 1200 |
| tactcattac | aggatgtagg | cggagatgcc | aattggcagt | tggttgtaga | agaaggagaa | 1260 |
| atgaaggtat | acagaagaga | agtagaagaa | atgggattg | ttctggatcc | tttaaaagct | 1320 |
| acccatgcag | ttaaaggcgt | cacaggacat | gaagtctgca | attatttctg | gaatgttgac | 1380 |
| gttcgcaatg | actgggaaac | aactatagaa | actttcatg | tggtggaaac | attagctgat | 1440 |
| aatgcaatca | tcatttatca | aacacacaag | agggtgtggc | ctgcttctca | gcgagacgta | 1500 |
| ttatatcttt | ctgtcattcg | aaagatacca | gccttgactg | aaaatgaccc | tgaaacttgg | 1560 |
| atagtttgta | attttctgt | ggatcatgac | agtgctcctc | taaacaaccg | atgtgtccgt | 1620 |
| gccaaaataa | atgttgctat | gatttgtcaa | accttggtaa | gcccaccaga | gggaaaccag | 1680 |
| gaaattagca | gggacaacat | tctatgcaag | attacatatg | tagctaatgt | gaaccctgga | 1740 |
| ggatgggcac | cagcctcagt | gttaagggca | gtggcaaagc | gagagtatcc | taaatttcta | 1800 |
| aaacgtttta | cttcttacgt | ccaagaaaaa | actgcaggaa | agcctatttt | gttctagtat | 1860 |
| taacaggtac | tagaagatat | gttttatctt | tttttaactt | tatttgacta | atatgactg | 1919 |

<210> SEQ ID NO 2
<211> LENGTH: 23
<212> TYPE: DNA
<213> ORGANISM: Artificial
<220> FEATURE:

<223> OTHER INFORMATION: Primer CMV sense

<400> SEQUENCE: 2
gacgtcaatg ggagtttgtt ttg                                      23

<210> SEQ ID NO 3
<211> LENGTH: 22
<212> TYPE: DNA
<213> ORGANISM: Artificial
<220> FEATURE:
<223> OTHER INFORMATION: Primer Terminator anti-sense

<400> SEQUENCE: 3
caactagaag gcacagtcga gg                                       22

<210> SEQ ID NO 4
<211> LENGTH: 22
<212> TYPE: DNA
<213> ORGANISM: Artificial
<220> FEATURE:
<223> OTHER INFORMATION: Primer CERT-for

<400> SEQUENCE: 4
gcgttctgat ggtgacttct tg                                       22

<210> SEQ ID NO 5
<211> LENGTH: 22
<212> TYPE: DNA
<213> ORGANISM: Artificial
<220> FEATURE:
<223> OTHER INFORMATION: Primer CERT-rev

<400> SEQUENCE: 5
tgtcctgtga cgcctttaac tg                                       22

<210> SEQ ID NO 6
<211> LENGTH: 660
<212> TYPE: DNA
<213> ORGANISM: Artificial
<220> FEATURE:
<223> OTHER INFORMATION: 660bp PCR product CERT

<400> SEQUENCE: 6
gcgttctgat ggtgacttct tgcatagtac caacggcaat aaagaaaagt tatttccaca      60
tgtgacacca aaaggaatta atggtataga cttttaaggg gaagcgataa cttttaaagc     120
aactactgct ggaatccttg caacactttc tcattgtatt gaactaatgg ttaaacgtga     180
ggacagctgg cagaagagac tggataagga aactgagaag aaaagaagaa cagaggaagc     240
atataaaaat gcaatgacag aacttaagaa aaaatcccac tttggaggac agattatga     300 agaaggccct aacagtctga ttaatgaaga agagttcttt gatgctgttg aagctgctct     360
tgacagacaa gataaaatag aagaacagtc acagagtgaa aaggtgagat tacattggcc     420
tacatccttg ccctctggag atgccttttc ttctgtgggg acacatagat tgtccaaaa     480 ggttgaagag atggtgcaga accacatgac ttactcatta caggatgtag gcggagatgc     540
caattggcag ttggttgtag aagaaggaga aatgaaggta tacagaagag aagtagaaga     600
aaatgggatt gttctggatc ctttaaaagc tacccatgca gttaaaggcg tcacaggaca     660

CHO/CERT CELL LINES

BACKGROUND OF THE INVENTION

1. Technical Field

The invention concerns the field of cell culture technology, specifically production host cell lines containing vector constructs comprising a ceramide transfer protein (CERT) expression cassette. Those cell lines have improved secretion characteristics in comparison to non-transgenic cell lines.

2. Background

The market for biopharmaceuticals for use in human therapy continues to grow at a high rate with over 900 biopharmaceuticals being evaluated in clinical studies and estimated sales of 50 billions in 2010. Over the years, an increasing number of biopharmaceuticals is produced from mammalian cells due to their ability to correctly process and modify human is proteins. Successful and high yield production of biopharmaceuticals from mammalian cells is thus crucial and depends on the characteristics of the recombinant monoclonal cell line used in the process.

Since most biopharmaceutical products are proteins that are secreted from the cells during the production process, the secretory transport machinery of the production cell line is another interesting target for novel host cell engineering strategies.

Protein secretion is a complex multi-step mechanism: Proteins destined to be transported to the extracellular space or the outer plasma membrane are first co-translationally imported into the endoplasmic reticulum. From there, they are packed in lipid vesicles and transported to the Golgi apparatus and finally from the trans-Golgi network (TGN) to the plasma membrane where they are released into the culture medium.

Many engineering approaches have employed the growing understanding of the molecular networks that drive processes such as transcription and translation to increase the yield of these steps in protein production. However, as for any multi-step production process, widening a bottle-neck during early steps of the process chain possibly creates bottle necks further downstream, especially post translation. Up to a certain threshold, the specific productivity of a production cell has been reported to correlate linearly with the level of product gene transcription. Further enhancement of product expression at the mRNA level, however, may lead to an overload of the protein synthesis, folding or transport machinery, resulting in intracellular accumulation of the protein product. Indeed, this can be frequently observed in current manufacturing processes.

Therefore, there is a need for improving the secretory capacity of host cells for recombinant protein production. This might even become more important in combination with novel transcription-enhancing technologies and in high-titer processes in order to prevent post-translational bottle necks and intracellular accumulation of the protein product.

However, previous approaches to target the post-translational machinery, have not succeeded but rather led to contradictory results depending on cell line or product used in the study or the initial productivity level:

Overexpression of the ER-resident molecular chaperone BiP (binding protein BiP/GRP78) unexpectedly resulted in reduced secretion;

Enhanced expression of the enzyme protein disulfide isomerase (PDI) showed contradictory results.

Secretion engineering using the transcription factor X-box binding protein 1 (XBP-1) was observed to either have no effect or to enhance secretion, however, apoptotic cell death was increased concomitantly, leading to an instable phenotype and preventing the isolation of XBP-1 high-expressing clones.

Thus, at present, there are two major hurdles on the way to targeted manipulation of the secretory transport machinery: The still limited knowledge about the underlying regulatory mechanisms and the requirement to prevent a concomitant growth-inhibitory or apoptotic response of the producer cell.

SUMMARY OF THE INVENTION

The present invention describes two specific novel production host cell lines CHO/CERT 2.20 and CHO/CERT 2.41. These two cell lines, which are deposited with the DSMZ s under the numbers DSM ACC2989 (CHO/CERT 2.20) and DSM ACC2990 (CHO/CERT 2.41) are ideal host cell lines for recombinant protein production as they have an improved secretory capacity as well as good growth characteristics.

We have recently shown that secretion engineering by overexpression of a protein from the steroidogenic acute regulatory related lipid transfer (START) domain family, preferably the ceramide transfer protein (CERT), provides a method to efficiently improve the production of proteins that are transported via the secretory pathway from eukaryotic cells. See Florin et al., 2009 and patent application WO2008/107388, which is hereby incorporated by reference.

CERT (also known as Goodpasture antigen-binding protein) is a cytosolic protein essential for the non-vesicular delivery of ceramide from its site of production at the endoplasmic reticulum (ER) to Golgi membranes, where conversion to sphingomyelin (SM) takes place (Hanada et al., 2003).

We could now demonstrate that the CERT mutant S132A, which bears a Ser→Ala point mutation and which is not phosphorylated by the protein kinase D any more, was significantly more effective in enhancing secretion than the wild type protein.

Furthermore, we now show that the CERT S132A expression level correlates with its secretion enhancing effect, meaning the higher the level of heterologous CERT S132A in the cell, the higher the secretory capacity of said cell (FIG. 2):

To investigate the correlation between CERT S132A expression level and specific antibody productivity we analysed two clonal cell lines with low and two with high expression levels of the CERT mutant, as judged by the signal intensities in intracellular FACS staining (FIG. 2A). In a seven-day fed-batch process, mock transfected control cell lines showed an average productivity of 15 pcd (FIG. 2B). The specific productivities of cell clones expressing low levels of the CERT SA mutant were only slightly elevated, whereas those clones with high levels of the CERT mutant secreted about 23 pcd of the IgG product and thus showed clearly increased specific productivities compared to mock controls (FIG. 2B). These data show that a correlation exists between the positive effect on recombinant protein secretion and the level of CERT S132A overexpression.

Furthermore, we surprisingly show that the selected cell clones CHO/CERT S132A 2.20 and CHO/CERT S132A 2.41 grow markedly better than the other clones and even better than the parental CHO wildtype cell line (FIGS. 5A and B).

Good growth characteristics are especially important for a production host cell line, since a low growth capacity has a negative impact on multiple aspects of the biopharmaceutical production process by causing:

Prolonged generation times of cells, which results in prolonged time lines in cell line development Lower efficiency after single cell cloning and slower growth thereafter Longer timeframes during scale up, especially in the case of inocculum for a production fermenter at large scale Lower product yield per fermenter run.

Thus, the specific problem solved by the present invention is to create a CERT S132A-engineered host cell line that exhibits both:

High expression levels of the CERT mutant S132A and optimal cell growth.

The present invention describes the generation of two such engineered CHO/CERT S132A cell lines with optimized secretion and good growth properties. The monoclonal cell lines provided in this invention are particularly useful as optimized host cell systems with enhanced production capacity for the expression and manufacture of recombinant protein products.

The two cell lines were generated by transfection of the CHO-DG44 host cell line with an expression construct encoding the human CERT S132A protein and subsequent selection to generate stable cell pools. From these, monoclonal cell lines were obtained by FACS-based single-cell cloning and subjected to extensive screening and characterization. In total, more than 100 clones were analysed and finally, the two CHO/CERT S132A cell lines 2.20 and 2.41 were selected based on:

high levels of CERT expression as determined by intracellular staining and Western Blotting good growth in seed stock cultures (viability, doubling time) as well as optimal growth in fed batch cultures reflecting the industrial production process (peak cell density, integral of viable cells over time (IVC), viability)

As the cell lines described in this invention only contain puromycin as selection marker, they are compatible with the most widely used selection- and amplification systems DHFR, glutamine synthetase (GS) and Neomycin (Neo) and thus can be used for expression of recombinant antibodies without adaptations/changes in the design of expression systems.

From over 100 CHO/CERT S132A clones generated, we selected in particular two novel monoclonal CHO-DG44 derived cell lines according to these criteria, namely clone 2.20 and clone 2.41, which are deposited with the Deutsche Sammlung von Mikroorganismen und Zellkulturen GmbH (DSMZ), Inhoffenstr. 7B, D-38124, Braunschweig, under the accession numbers DSM ACC2989 and DSM ACC2990 (date of deposit April 2, 2009):

The cell line, which we call "CHO/CERT 2.20" and which is deposited with the DSMZ under the number DSM ACC2989, has a very high CERT S132A expression level and very good growth characteristics, which are even better than those of the parental CHO wildtype cell.

This cell line can be uniquely described by identifying junction fragments between the inserted DNA and the adjacent chromosomal DNA of cells of the cell line. For example, DNA of the cell line is digested with one or more restriction enzymes and such junction fragments are identified, e.g by Southern blot analysis using a suitable labelled fragment of the inserted DNA, leading to a specific band pattern identifying the insertion site in the genome. Such restriction enzymes for example described hereinafter and include EcoRV, HindIII, KpnI, NcoI, NdeI, PvuII, SpeI, XhoI, AvaII, BstXI, SalI.

The cell line, which we call "CHO/CERT 2.41" and which is deposited with the DSMZ under the number DSM ACC2990, has a very high CERT S132A expression level and very good growth characteristics, which are even better than those of the parental CHO wildtype cell.

This cell line can be uniquely described by identifying junction fragments between the inserted DNA and the adjacent chromosomal DNA of cells of the cell line. For example, DNA of the cell line is digested with one or more restriction enzymes and such junction is fragments are identified, e.g by Southern blot analysis using a suitable labelled fragment of the inserted DNA, leading to a specific band pattern identifying the insertion site in the genome. Such restriction enzymes for example described hereinafter and include EcoRV, HindIII, KpnI, NcoI, NdeI, PvuII, SpeI, XhoI, AvaII, BstXI, SalI.

The present invention thus describes especially a cell line deposited with the DSMZ under the number DSM ACC2989 and another cell line deposited with the DSMZ under the number DSM ACC2990. For the purpose of this application these two cell lines are also called "conCERT™" cell lines.

Compared to the parental CHO-DG44 cell line, these two cell lines show increased secretion rates of therapeutic protein products following transfection with the corresponding expression plasmids as well as good growth characteristics. They integrate the advantages of the CHO-DG44 host cell line (being well characterized, FDA-approved, low risk of viral burden, high productivity, robustness, transfectability, growth in suspension in serum-free medium) with the new property of enhanced secretion and optimized performance in production processes.

The specific conCERT™ cell lines exemplary described in the present invention contain an expression cassette encoding the flag-tagged human CERT mutant S132A as depicted in FIGS. 1A and B (SEQ ID NO: 1) comprising upstream regulatory sequences (600 bp) derived from the cytomegalovirus (CMV) promoter/enhancer region, the N-terminal Flag-epitope tag fused to the human CERT cDNA bearing a point mutation at position 132 (Ser 132→Ala), a stop codon and a 3' untranslated region including polyadenylation signal.

The vector construct used for generation of the conCERT™ cell lines described in the present invention is shown in FIG. 1B and contains the following functional elements:

Cytomegalovirus (CMV) enhancer/promoter, multiple cloning site (MCS), polyadenylation signal, CERT S132A expression cassette, expression cassette encoding the puromycin N-acetyl transferase as selection marker in eukaryotic cells, origin of replication, and beta-lactamase expression cassette for ampicillin resistance in bacteria.

Antibody concentrations in conCERT™ cell lines are significantly higher compared to the titers measured in stably transfected wild type cells, the average difference ranging from 1.5-2.5-fold (FIG. 6). Thus, conCERT™ cell lines yield significantly higher product titers than wild type CHO cells in a side-by-side comparison. These data demonstrate that the CHO/CERT S132A cells deposited with the DSMZ under the numbers DSM ACC2989 (CHO/CERT 2.20) and DSM ACC2990 (CHO/CERT 2.41) are superior host cells for recombinant protein production compared to the parental DG44 cell line. Specific examples of conCERT™ cells as host cells for recombinant protein production are given for IgG4- and IgG1-subtype antibodies, Fc-fusion proteins, single-chain-Fv (scFv) molecules and nanobodies). But conCERT™ cells are also preferred host cell for recombinant protein production of other proteins, polypeptides or fragments thereof such as enzymes, cytokines, lymphokines, structural molecules, adhesion molecules, receptors and derivatives or fragments thereof, as well as other polypeptides that can serve as agonists or antagonists and/or have therapeutic or diagnostic use.

The cell lines provided by this invention will enable to increase the protein yield in production processes based on eukaryotic cells. This will reduce the cost of goods of such processes and at the same time reduce the number of batches that need to be produced to generate the material needed for research studies, diagnostics, clinical studies or market supply of a therapeutic protein.

The conCERT™ cell lines of the present invention will furthermore speed up drug development as often the generation of sufficient amounts of material for pre-clinical studies is a critical work package with regard to the timeline.

The optimized conCERT™ cell lines of the present invention can be used for the is generation of one or several specific proteins for either diagnostic purposes, research purposes (target identification, lead identification, lead optimization) or manufacturing of therapeutic proteins either on the market or in clinical development. They are equally applicable to express or produce secreted or membrane-bound proteins (such as surface receptors, GPCRs, metalloproteases or receptor kinases) which share the same secretory pathways and are equally transported in lipid-vesicles. The proteins can then be used for research purposes which aim to characterize the function of cell-surface receptors, e.g. for the production and subsequent purification, crystallization and/or analysis of surface proteins. This is of crucial importance for the development of new human drug therapies as cell-surface receptors are a predominant class of drug targets. Moreover, it might be advantageous for the study of intracellular signalling complexes associated with cell-surface receptors or the analysis of cell-cell-communication which is mediated in part by the interaction of soluble growth factors with their corresponding receptors on the same or another cell.

(B) Map of the vector construct transfected into CHO-DG44 cells to generate the CHO/CERT S132A (conCERT™) cell lines described in the present invention.

The plasmid was internally designated "pBIP-1/Flag-CERT_SA" and has a size of 7660 bp. Black arrowheads indicate binding positions of oligonucleotide primers suited for identification of the conCERT™ cell lines. CMV=enhancer/promoter of the is cytomegalovirus (CMV) early region, followed by a multiple cloning site (indicated by unique recognition sites for the indicated enzymes); F1 ori=origin for replication in bacteria; bla=beta-lactamase gene for ampicillin resistance.

Figure 2:
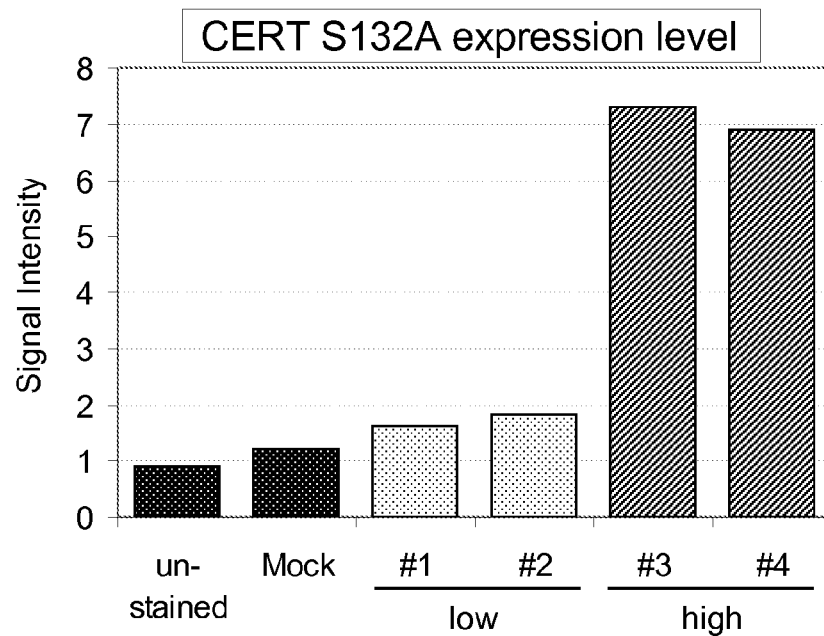
Figure 2:
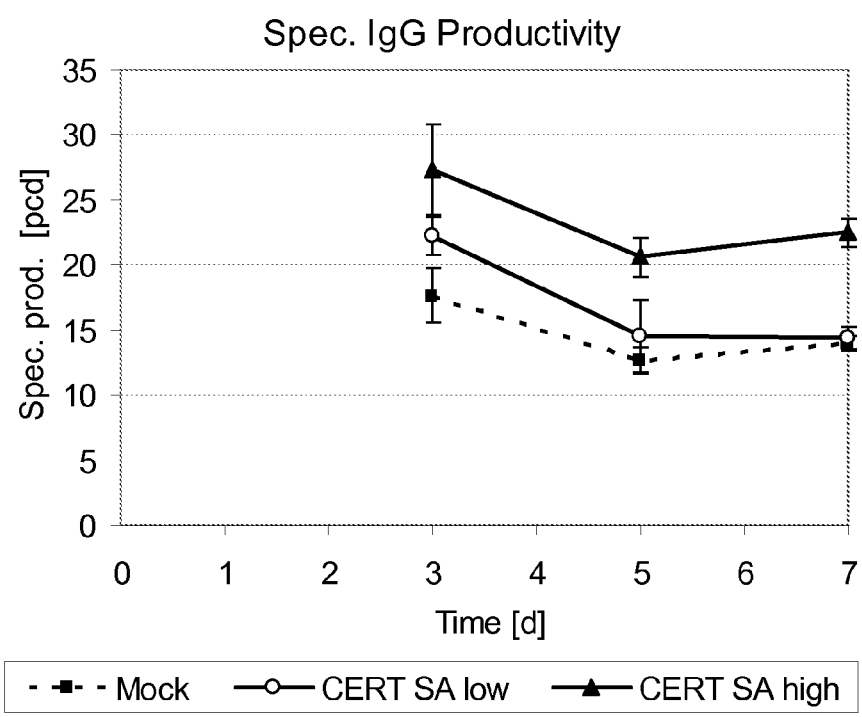

FIG. 2: CORRELATION OF CERT S132A EXPRESSION AND SECRETION ENHANCEMENT (A) Heterologous CERT S132A expression in IgG producing cell lines was measured by intracellular labelling with anti-Flag antibodies. Based on signal intensity, clones #1-2 were classified as "low" (light grey dotted bars), clones #3-4 as cell lines with "high" CERT-S132A expression (striped bars).

(B) Specific antibody productivity of the same cell lines in fed-batch cultures. The productivities of all cell lines were calculated at three time points during the process as product concentration divided by IVC (integral of viable cells).

FIG. 3: DETECTION OF CERT EXPRESSION BY WESTERN BLOTTING

Whole cell lysates were prepared from 14 CHO/CERT S132A cell clones and equal amounts were subjected to SDS-PAGE and subsequent immunologic detection using antibodies raised against the Flag™ epitope tag.

A number of 14 cell clones is displayed on the SDS-PAGE. The individual cell lines are designated by their clone numbers. M=molecular weight marker; (−)=negative control (lysates from mock transfected cell lines); (+)=positive control.

Figure 4:
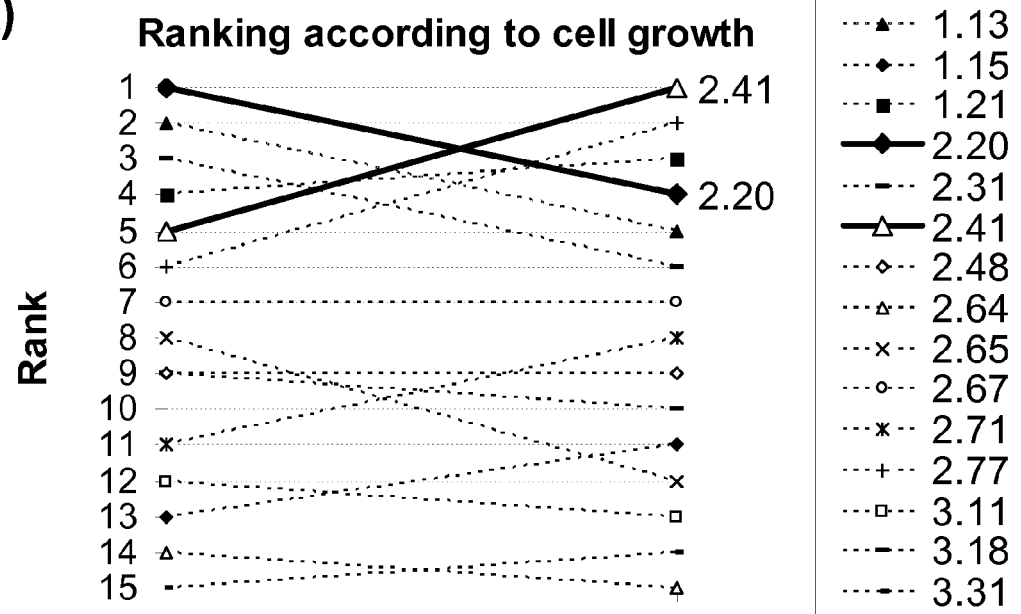
Figure 4:
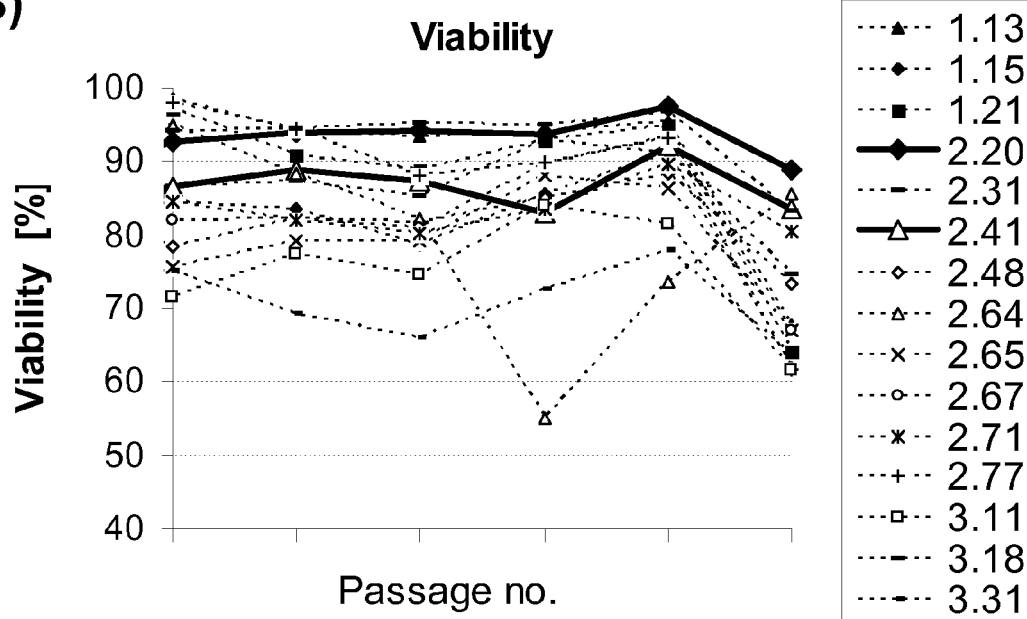

FIG. 4: GROWTH PROPERTIES OF CHO/CERT S132A (conCERT™) CELL LINES IN INOCULUM CULTURES Growth characteristics of 15 CHO/CERT S132A cell clones during inoculum cultivation. Cells were maintained at cell densities between $0.15\text{-}3\times10^6$ cells/ml and splitted every 2-3 days.

(A) Ranking of the cell lines according to growth rate. (B) Viabilities over several is passages; The cell lines deposited with the DSMZ under accession number DSM ACC2989 (CHO/CERT S132A 2.20) and DSM ACC2990 (CHO/CERT S132A 2.41) are indicated by solid lines, all other clones by dashed lines.

Figure 5:
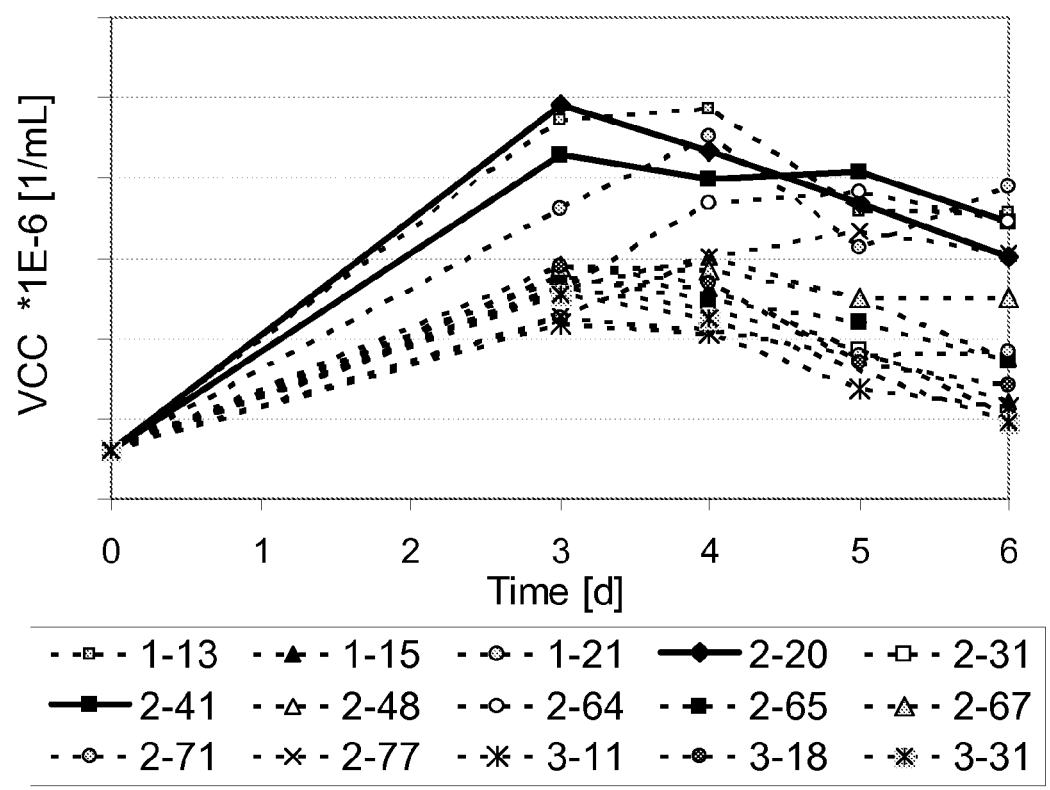
Figure 5:
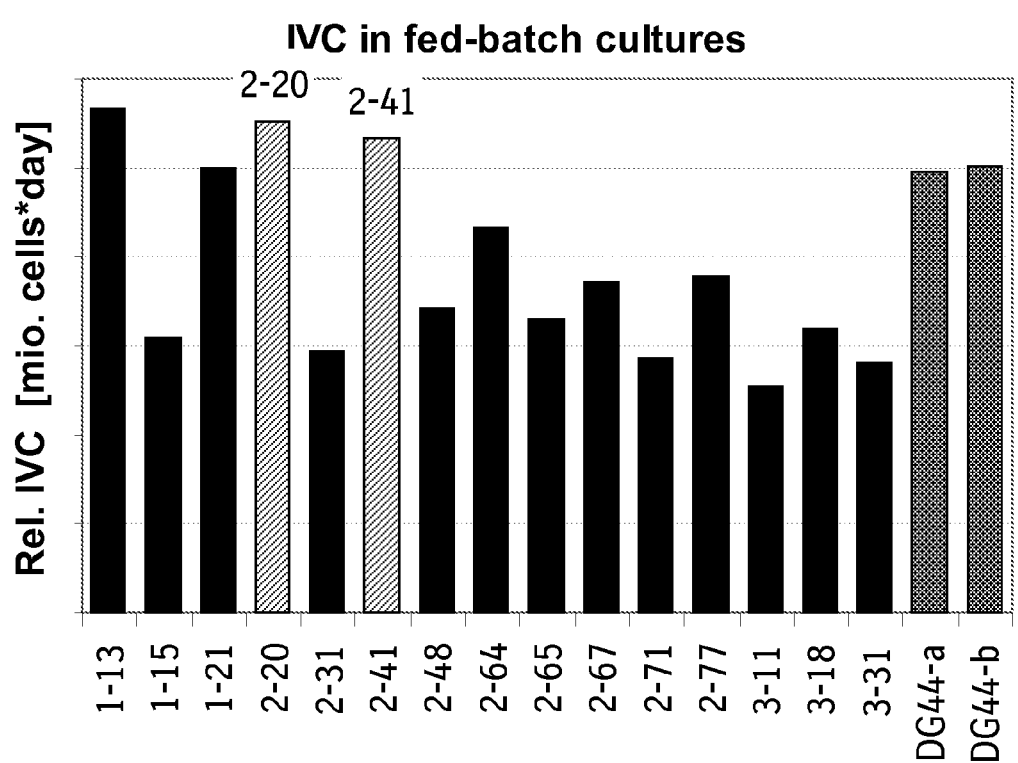

FIG. 5: GROWTH OF MONOCLONAL CHO/CERT S132A CELL LINES DURING FERMENTATION 15 monoclonal stably transfected CHO/CERT S132A cell clones were subjected to fed-batch fermentation over six days.

(A) Growth profiles of CHO/CERT S132A cell lines and the parental DG44 cell. The cell lines deposited with the DSMZ under accession number DSM ACC2989 (CHO/CERT 2.20) and DSM ACC2990 (CHO/CERT 2.41) are indicated by solid lines, all other clones by dashed lines.

(B) Integral of viable cell concentrations (IVC) for all cell lines over the six day process. IVCs of CHO/CERT S132A cell lines selected in the present invention are indicated by stripped bars, IVCs of the other CHO/CERT S132A clones are presented by black bars, IVCs of parental cells are represented in hatched bars.

Figure 6:
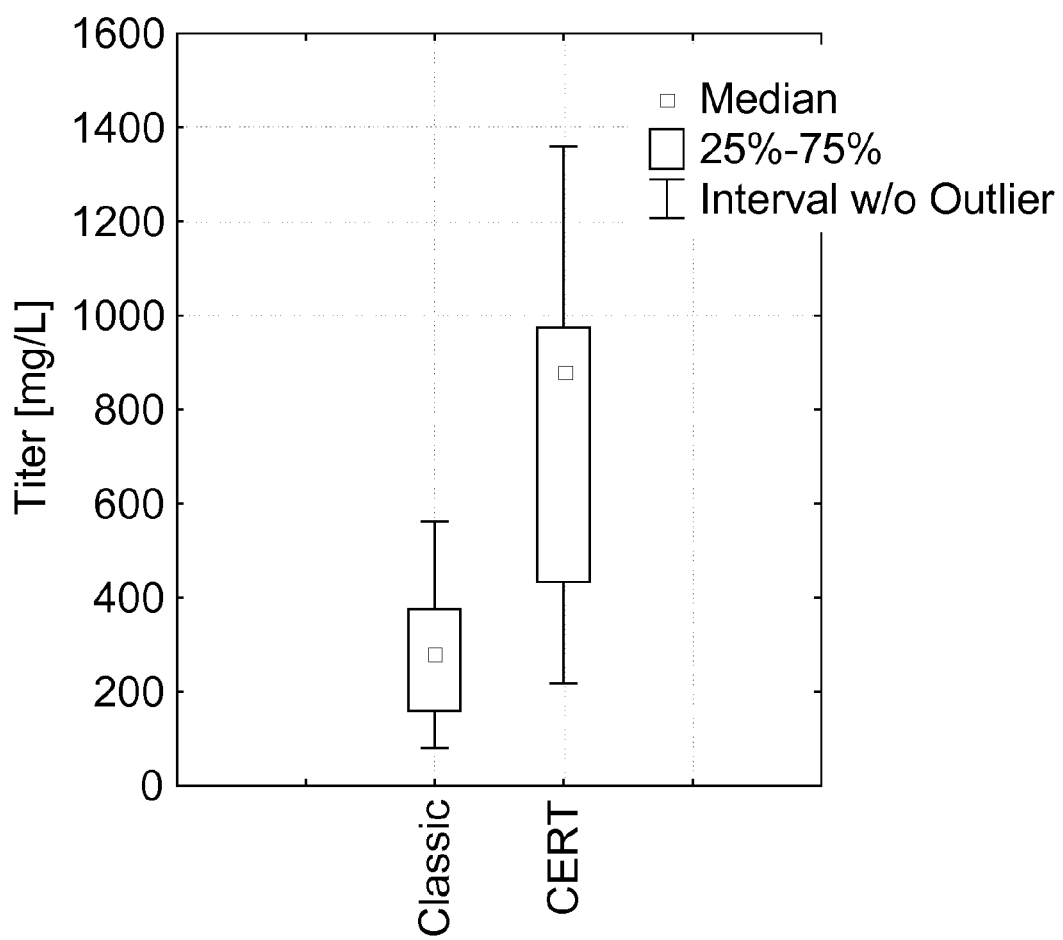

FIG. 6: COMPARISON OF ANTIBODY TITERS/PROTEIN PRODUCTION SECRETED FROM CHO/CERT S132A CELLS IN COMPARISON TO THE PARENTAL CHO DG44 CELL LINE

The conCERT™ cell lines deposited with the DSMZ under accession number DSM ACC2989 (CHO/CERT 2.20) and DSM ACC2990 (CHO/CERT 2.41) as well as the parental CHO-DG44 host cell line (Classic) are transfected with expression constructs encoding a human IgG1-type monoclonal antibody.

Antibody titers of the 10 highest expressing cell pools per genotype are presented in a box plot depicting median titer and 25-75% quantile as boxes. Error bars indicate standard deviations.

Figure 7:
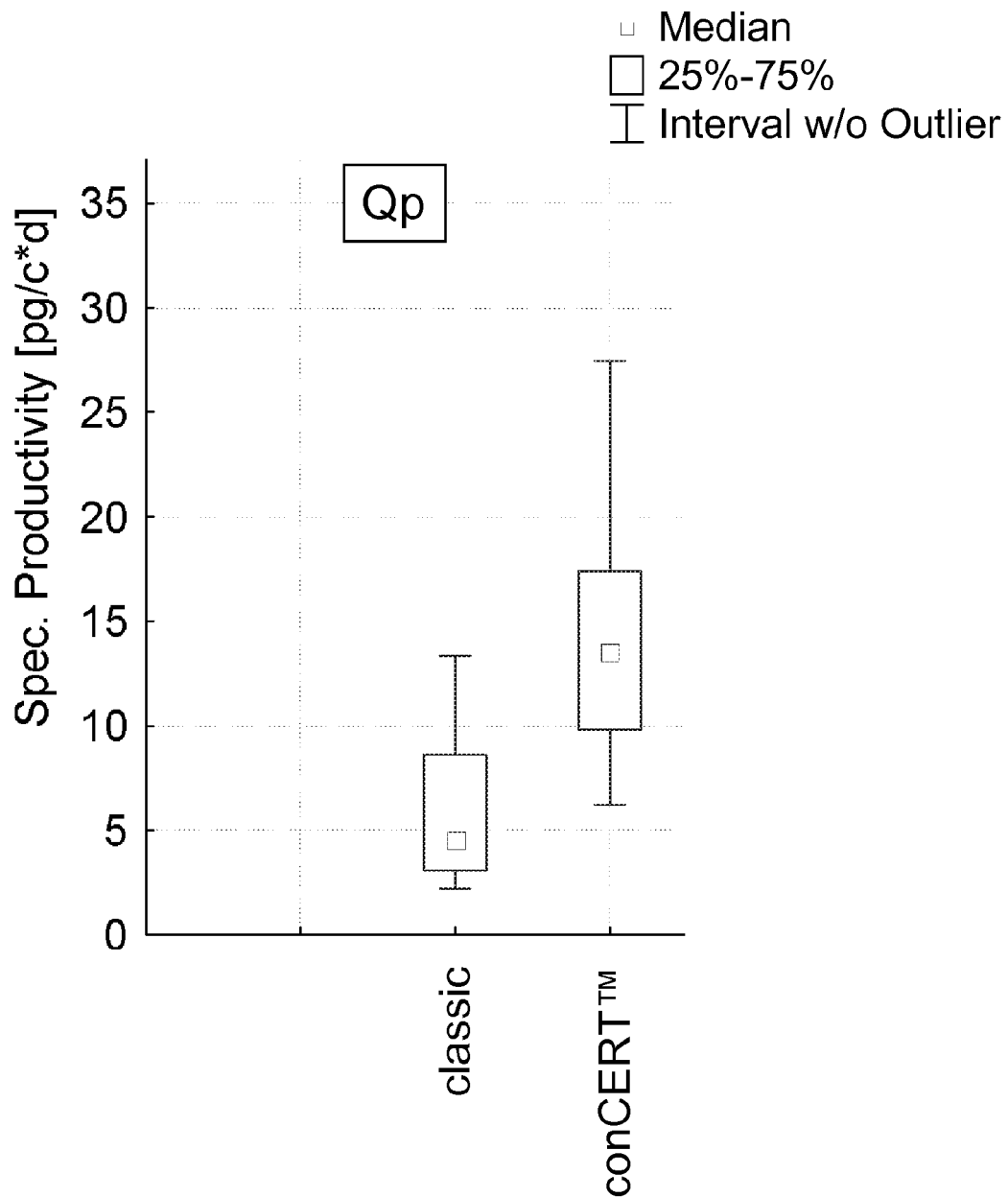
Figure 7:
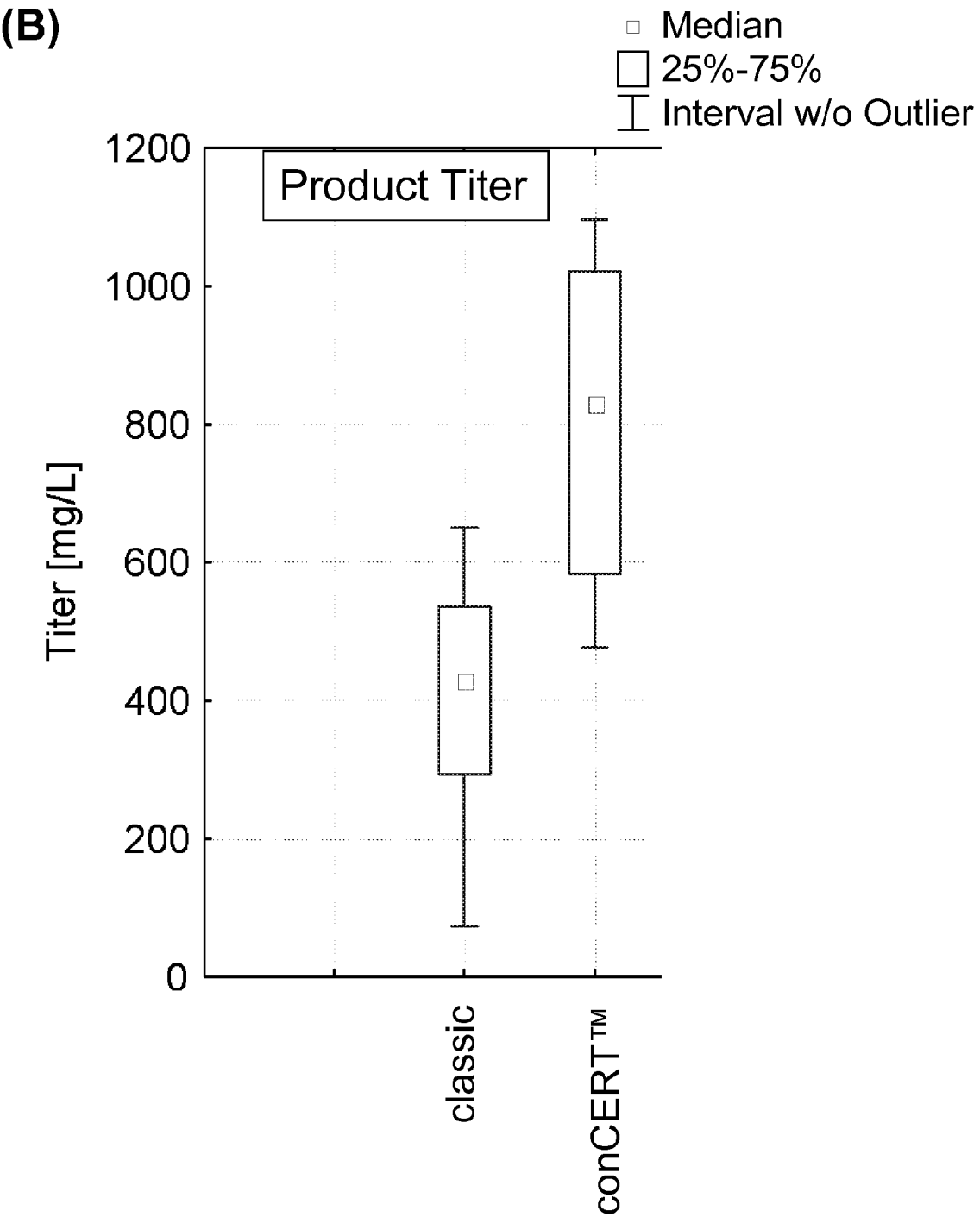

FIG. 7: COMPARISON OF ANTIBODY TITERS/PROTEIN PRODUCTION SECRETED FROM CHO/CERT S132A CELLS IN COMPARISON TO THE is PARENTAL CHO DG44 CELL LINE

The conCERT™ cell lines deposited with the DSMZ under accession number DSM ACC2989 (CHO/CERT 2.20) and DSM ACC2990 (CHO/CERT 2.41) as well as the parental CHO-DG44 host cell line (Classic) are transfected with expression constructs encoding a human IgG4-type monoclonal antibody. The 10 highest expressing cell pools per genotype are selected.

(A,B) Specific productivities (A) and antibody titres (B) of the 10 highest expressing monoclonal cell lines generated from the cell pools for each genotype are presented in a box plot depicting median titer and 25-75% quantile as boxes. Error bars indicate standard deviations.

DETAILED DESCRIPTION OF THE INVENTION

Definitions

The general embodiments "comprising" or "comprised" encompass the more specific embodiment "consisting of". Furthermore, singular and plural forms are not used in a limiting way.

Terms used in the course of this present invention have the following meaning

The term "CERT" refers to the ceramide transfer protein CERT, which is also known as Goodpasture antigen-binding protein. CERT is a cytosolic protein essential for the non-vesicular delivery of ceramide from its site of production at the endoplasmic reticulum (ER) to Golgi membranes, where conversion to sphingomyelin (SM) takes place (Hanada et al., 2003).

The terms "CHO/CERT", "CHO/CERT SA", "CHO/CERT S 132A" are used interchangeably. Furthermore, the cell line designations "CHO/CERT 2.20", "CHO/CERT SA 2.20", "CHO/CERT S132A 2.20" are used interchangeably and all of them describe the same cell line clone 2.20, deposited under the Accession Number DSMZ DSM ACC2989. The cell line designations "CHO/CERT 2.41", "CHO/CERT SA 2.41", "CHO/CERT S132A 2.41" are used interchangeably and all of them describe the same cell line clone 2.41, deposited under the Accession Number DSMZ DSM ACC2990.

The term "derivative" in general includes sequences suitable for realizing the intended use of the present invention, which means that the sequences mediate the increase in secretory transport in a cell.

"Host cells" in the meaning of the present invention are cells such as hamster cells, preferably BHK21, BHK TK⁻, CHO, CHO-K1, CHO-DUKX, CHO-DUKX B1, and CHO-DG44 cells or the derivatives/progenies of any of such cell line. Particularly preferred are CHO-DG44, CHO-DUKX, CHO-K1, CHO-S and BHK21, and even more preferred CHO-DG44 and CHO-DUKX cells. In a further embodiment of the present invention host cells also mean murine myeloma cells, preferably NS0 and Sp2/0 cells or the derivatives/progenies of any of such cell line. Examples of murine and hamster cells which can be used in the meaning of this invention are also summarized in Table 1. However, derivatives/progenies of those cells, other mammalian cells, including but not limited to human, mice, rat, monkey, and avian or preferably rodent cell lines, or eukaryotic cells, including but not limited to yeast, insect and plant cells, can also be used in the meaning of this invention, particularly for the production of biopharmaceutical proteins.

TABLE 1

Eukaryotic production cell lines

| CELL LINE | ORDER NUMBER |
| --- | --- |
| NS0 | ECACC No. 85110503 |
| Sp2/0-Ag14 | ATCC CRL-1581 |
| BHK21 | ATCC CCL-10 |
| BHK TK⁻ | ECACC No. 85011423 |
| HaK | ATCC CCL-15 |
| 2254-62.2 (BHK-21 derivative) | ATCC CRL-8544 |

TABLE 1-continued

Eukaryotic production cell lines

| CELL LINE | ORDER NUMBER |
| --- | --- |
| CHO | ECACC No. 8505302 |
| CHO wild type | ECACC 00102307 |
| CHO-K1 | ATCC CCL-61 |
| CHO-DUKX (=CHO duk⁻, CHO/dhfr⁻) | ATCC CRL-9096 |
| CHO-DUKX B11 | ATCC CRL-9010 |
| CHO-DG44 | Urlaub et al., 1983 |
| CHO Pro-5 | ATCC CRL-1781 |
| V79 | ATCC CCC-93 |
| B14AF28-G3 | ATCC CCL-14 |
| PER.C6 | (Fallaux, F. J. et al, 1998) |
| HEK 293 | ATCC CRL-1573 |
| COS-7 | ATCC CRL-1651 |
| U266 | ATCC TIB-196 |
| HuNS1 | ATCC CRL-8644 |
| CHL | ECACC No. 87111906 |

Host cells are most preferred, when being established, adapted, and completely cultivated under serum free conditions, and optionally in media which are free of any protein/peptide of animal origin. Commercially available media such as Ham's F12 (Sigma, Deisenhofen, s Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif.), CHO-S-Invtirogen), serum-free CHO Medium (Sigma), and protein-free CHO Medium (Sigma) are exemplary appropriate nutrient solutions. Any of the media may be supplemented as necessary with a variety of compounds examples of which are hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics, trace elements. Any other necessary supplements may also be included at appropriate concentrations that would be known to those skilled in the art. In the present invention the use of serum-free medium is preferred, but media supplemented with a suitable amount of serum can also be used for the cultivation of host cells. For the growth and selection of genetically modified cells expressing the selectable gene a suitable selection agent is added to the culture medium.

The term "protein" is used interchangeably with amino acid residue sequences or polypeptide and refers to polymers of amino acids of any length. These terms also include proteins that are post-translationally modified through reactions that include, but are not limited to, glycosylation, acetylation, phosphorylation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with like properties.

The term "polypeptide" means a sequence with more than 10 amino acids and the term "peptide" means sequences up to 10 amino acids length.

The present invention is suitable to generate host cells for the production of biopharmaceutical polypeptides/proteins. The invention is particularly suitable for the high-yield expression of a large number of different genes of interest by cells showing an enhanced cell productivity.

"Gene of interest" (GOI), "selected sequence", or "product gene" have the same meaning herein and refer to a polynucleotide sequence of any length that encodes a product of interest or "protein of interest", also mentioned by the term "desired product". The selected sequence can be full length or a truncated gene, a fusion or tagged gene, and can be a cDNA, a genomic DNA, or a DNA fragment, preferably, a cDNA. It can be the native sequence, i.e. naturally occurring form(s), or can be mutated or otherwise modified as desired. These modifications include codon optimizations to optimize codon usage in the selected host cell, humanization or tagging. The selected sequence can encode a secreted, cytoplasmic, nuclear, membrane bound or cell surface polypeptide.

The "protein of interest" includes proteins, polypeptides, fragments thereof, peptides, all of which can be expressed in the selected host cell. Desired proteins can be for example antibodies, enzymes, cytokines, lymphokines, adhesion molecules, receptors and derivatives or fragments thereof, and any other polypeptides that can serve as agonists or antagonists and/or have therapeutic or diagnostic use. Examples for a desired protein/polypeptide are also given below.

In the case of more complex molecules such as monoclonal antibodies the GOI encodes one or both of the two antibody chains.

The "product of interest" may also be an antisense RNA.

"Proteins of interest" or "desired proteins" are those mentioned above. Especially, desired proteins/polypeptides or proteins of interest are for example, but not limited to insulin, insulin-like growth factor, hGH, tPA, cytokines, such as interleukines (IL), e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosisfactor (TNF), such as TNF alpha and TNF beta, TNF gamma, TRAIL; G-CSF, GM-CSF, M-CSF, MCP-1 and VEGF. Also included is the production of erythropoietin or any other hormone growth factors. The method according to the invention can also be advantageously used for production of antibodies or fragments thereof. Such fragments include e.g. Fab fragments (Fragment antigen-binding =Fab). Fab fragments consist of the variable regions of both chains which are held together by the adjacent constant region. These may be formed by protease digestion, e.g. with papain, from conventional antibodies, but similar Fab fragments may also be produced in the mean time by genetic engineering. Further antibody fragments include F(ab')2 fragments, which may be prepared by proteolytic cleaving with pepsin.

The protein of interest is preferably recovered from the culture medium as a secreted polypeptide, or it can be recovered from host cell lysates if expressed without a secretory signal. It is necessary to purify the protein of interest from other recombinant proteins and host cell proteins in a way that substantially homogenous preparations of the protein of interest are obtained. As a first step, cells and/or particulate cell debris are removed from the culture medium or lysate. The product of interest thereafter is purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin such as DEAE. In general, methods teaching a skilled person how to purify a protein heterologous expressed by host cells, are well known in the art.

Using genetic engineering methods it is possible to produce shortened antibody fragments which consist only of the variable regions of the heavy (VH) and of the light chain (VL). These are referred to as Fv fragments (Fragment variable=fragment of the variable part). Since these Fv-fragments lack the covalent bonding of the two chains by the cysteines of the constant chains, the Fv fragments are often stabilised. It is advantageous to link the variable regions of the heavy and of the light chain by a short peptide fragment, e.g. of 10 to 30 amino acids, preferably 15 amino acids. In this way a single peptide strand is obtained consisting of VH and VL, linked by a peptide linker. An antibody protein of this kind is known as a single-chain-Fv (scFv). Examples of scFv-antibody proteins of this kind known from the prior art.

In recent years, various strategies have been developed for preparing scFv as a multimeric derivative. This is intended to lead, in particular, to recombinant antibodies with improved pharmacokinetic and biodistribution properties as well as with increased binding avidity. In order to achieve multimerisation of the scFv, scFv were prepared as fusion proteins with multimerisation domains. The multimerisation domains may be, e.g. the CH3 region of an IgG or coiled coil structure (helix structures) such as Leucin-zipper domains. However, there are also strategies in which the interaction between the VH/VL regions of the scFv are used for the multimerisation (e.g. dia-, tri- and pentabodies). By diabody the skilled person means a bivalent homodimeric scFv derivative. The shortening of the Linker in an scFv molecule to 5-10 amino acids leads to the formation of homodimers in which an inter-chain VH/VL-superimposition takes place. Diabodies may additionally be stabilised is by the incorporation of disulphide bridges. Examples of diabody-antibody proteins are known in the prior art.

By minibody the skilled person means a bivalent, homodimeric scFv derivative. It consists of a fusion protein which contains the CH3 region of an immunoglobulin, preferably IgG, most preferably IgG1 as the dimerisation region which is connected to the scFv via a Hinge region (e.g. also from IgG1) and a Linker region. Examples of minibody-antibody proteins are known in the prior art.

By triabody the skilled person means a: trivalent homotrimeric scFv derivative. ScFv derivatives wherein VH-VL are fused directly without a linker sequence lead to the formation of trimers.

The skilled person will also be familiar with so-called miniantibodies which have a bi-, tri- or tetravalent structure and are derived from scFv. The multimerisation is carried out by di-,tri- or tetrameric coiled coil structures.

The person skilled in the art will also be familiar with polypeptide molecules which consist of one or more variable domains of the single-chain antibody derived from lamas or other animals from the family of camelidae. Furthermore, the person skilled in the art is aware of derivatives and variants of such camelidae antibodies. Such molecules are also referred to as "domain antibodies". Domain antibody variants include several of those variable domains which are covalently connected by a peptide linker.

To increase serum half-life, domain antibodies can be generated which are fused to a polypeptide moiety such as an antibody Fc-part or another protein present in the blood serum such as albumin.

By "scaffold proteins" a skilled person means any functional domain of a protein that is coupled by genetic cloning or by co-translational processes with another protein or part of a protein that has another function.

By definition any sequences or genes introduced into a host cell are called "heterologous sequences" or "heterologous genes" or "transgenes" with respect to the host cell, even if the introduced sequence or gene is identical to an endogenous sequence or gene in the host cell.

A "heterologous" protein is thus a protein expressed from a heterologous sequence.

The term "recombinant" is used exchangeably with the term "heterologous" throughout the specification of this present invention, especially in the context with protein expression.

Thus, a "recombinant" protein is a protein expressed from a heterologous sequence.

Heterologous gene sequences can be introduced into a target cell by using an "expression vector", preferably an eukaryotic, and even more preferably a mammalian expression vector. Methods used to construct vectors are well known to a person skilled in the art and described in various publications. In particular techniques for constructing suitable vectors, including a description of the functional components such as promoters, enhancers, termination and polyadenylation signals, selection markers, origins of replication, and splicing signals, are reviewed in the prior art. Vectors may include but are not limited to plasmid vectors, phagemids, cosmids, articificial/mini-chromosomes (e.g. ACE), or viral vectors such as baculovirus, retrovirus, adenovirus, adeno-associated virus, herpes simplex virus, retroviruses, bacteriophages. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operatively linked, are well known in the art and some are commercially available from companies such as Stratagene, La Jolla, Calif.; Invitrogen, Carlsbad, Calif.; Promega, Madison, Wis. or BD Biosciences Clontech, Palo Alto, Calif.

In a preferred embodiment the expression vector comprises at least one nucleic acid sequence which is a regulatory sequence necessary for transcription and translation of nucleotide sequences that encode for a peptide/polypeptide/protein of interest.

The term "expression" as used herein refers to transcription and/or translation of a heterologous nucleic acid sequence within a host cell. The level of expression of a desired product/protein of interest in a host cell may be determined on the basis of either the amount of corresponding mRNA that is present in the cell, or the amount of the desired polypeptide/protein of interest encoded by the selected sequence as in the present examples. For example, mRNA transcribed from a selected sequence can be quantitated by Northern blot hybridization, ribonuclease RNA protection, in situ hybridization to cellular RNA or by PCR. Proteins encoded by a selected sequence can be quantitated by various methods, e.g. by ELISA, by Western blotting, by radioimmunoassays, by immunoprecipitation, by assaying for the biological activity of the protein, by immunostaining of the protein followed by FACS analysis or by homogeneous time-resolved fluorescence (HTRF) assays.

"Transfection" of eukaryotic host cells with a polynucleotide or expression vector, resulting in genetically modified cells or transgenic cells, can be performed by any method well known in the art. Transfection methods include but are not limited to liposome-mediated transfection, calcium phosphate co-precipitation, electroporation, polycation (such as DEAE-dextran)-mediated transfection, protoplast fusion, viral infections and microinjection. Preferably, the transfection is a stable transfection. The transfection method that provides optimal transfection frequency and expression of the heterologous genes in the particular host cell line and type is favoured. Suitable methods can be determined by routine procedures. For stable transfectants the constructs are either integrated into the host cell's genome or an artificial chromosome/mini-chromosome or located episomally so as to be stably maintained within the host cell.

The practice of the present invention will employ, unless otherwise indicated, conventional techniques of cell biology, molecular biology, cell culture, immunology and the like which are in the skill of one in the art. These techniques are fully disclosed in the current literature.

Embodiments

The invention relates to a cell deposited with the DSMZ (Deutsche Sammlung von is Mikroorganismen und Zellkulturen GmbH) under the number DSM ACC2989 (CHO/CERT 2.20). The invention relates to a cell/cell line, a representative of which is deposited with the DSMZ under the number DSM ACC2989 (CHO/CERT 2.20). This cell line can be uniquely described by identifying junction fragments between the inserted DNA and the adjacent chromosomal DNA of cells of the cell line. For example, DNA of the cell line is digested with one or more restriction enzymes and such junction fragments are identified, e.g by Southern blot analysis using a suitable labelled fragment of the inserted DNA, leading to a specific band pattern identifying the insertion site in the genome. Such restriction enzymes for example described hereinafter and include EcoRV, HindIII, KpnI, NcoI, NdeI, PvuII, SpeI, XhoI, AvaII, BstXI, SalI.

The invention further relates to a cell deposited with the DSMZ under the number DSM ACC2990 (CHO/CERT 2.41). The invention relates to a cell/cell line, a representative of which is deposited with the DSMZ under the number DSM ACC2990 (CHO/CERT 2.41). This cell line can be uniquely described by identifying junction fragments between the inserted DNA and the adjacent chromosomal DNA of cells of the cell line. For example, DNA of the cell line is digested with one or more restriction enzymes and such junction fragments are identified, e.g by Southern blot analysis using a suitable labelled fragment of the inserted DNA, leading to a specific band pattern identifying the insertion site in the genome. Such restriction enzymes for example described hereinafter and include EcoRV, HindIII, KpnI, NcoI, NdeI, PvuII, SpeI, XhoI, AvaII, BstXI, SalI.

In a specific embodiment of the present invention the inventive cell (CHO/CERT 2.20 or CHO/CERT 2.41) additionally contains at least one second vector construct comprising a gene of interest encoding a protein of interest. Said cell preferably additionally contains at least one second vector construct comprising a gene of interest encoding a protein of interest and a selection and/or amplification marker. Said selection and/or amplification marker on the second vector construct is preferably glutamine synthetase (GS) or dehydrofolate reductase (DHFR), most preferably DHFR.

In a further preferred embodiment of the present invention all vector constructs are stably integrated into the cells genome.

In a further preferred embodiment of the present invention said cell is characterized by a specific PCR band pattern/fingerprint when using genomic DNA as template, whereby a 2373 bp PCR product is generated using the oligonucleotide primers of SEQ ID NO: 2 and SEQ ID NO:3 or a specific PCR band pattern/fingerprint when using genomic DNA as template, whereby a 660 bp PCR product (SEQ ID NO: 6) is generated using the oligonucleotide primers of SEQ ID NO: 4 and SEQ ID NO: 5 or a specific number of fragments and fragment sizes resulting from the incubation of the CERT-specific 2373 bp-PCR product of (a) with the following restriction enzymes:

| Enzyme | # Fragments | Fragment size (bps) |
|--------|-------------|---------------------|
| EcoRV  | 2           | 2236, 137           |
| HindIII | 2          | 2176, 197           |
| KpnI   | 2           | 2142, 231           |
| NcoI   | 2           | 2096, 277           |
| NdeI   | 2           | 1973, 400           |
| PvuII  | 2           | 1241, 1132          |
| SpeI   | 2           | 2128, 245           |
| XhoI   | 2           | 2257, 116           |
| AvaII  | 3           | 1140, 832, 401      |
| BstXI  | 3           | 1980, 266, 127      |
| SalI   | 3           | 1673, 491, 209      | whereby the incubation with HindIII is preferred.

In a preferred embodiment of the present invention said cell is characterized by 2 specific fragments with the sizes according to the above table resulting from the incubation of the CERT-specific 2373 bp PCR product, which is generated using genomic DNA as template and the oligonucleotide primers of SEQ ID NO: 2 and SEQ ID NO:3, with the following restriction enzymes: EcoRV, KpnI, NcoI, NdeI, PvuII, SpeI, XhoI.

In a most preferred embodiment of the present invention said cell is characterized by 2 specific fragments with the sizes 2176 bp and 197 bp, respectively, resulting from the incubation of the CERT-specific 2373 bp PCR product, which is generated using genomic DNA as template and the oligonucleotide primers of SEQ ID NO: 2 and SEQ ID NO:3 with the restriction enzyme HindIII.

In a specific embodiment of the present invention the CERT S132A expression cassette consists of the SEQ ID NO: 1.

In a further specific embodiment of the present invention the protein of interest is a therapeutic protein, preferably an antibody or an antibody fusion protein.

The invention further relates to a method for generating a host cell line characterized by the following steps
(a) Providing a parental host cell, preferably a CHO or NSO cell, most preferably a CHO DG44 cell,
(b) Introducing a vector construct in said cell of step (a) comprising a CERT S132A expression cassette,
(c) Selecting for a stably transfected cell population,
(d) Isolating monoclonal cell lines by FACS-based single-cell cloning,
(e) Screening for
high levels of CERT S132A expression,
optimal growth in seed stock cultures,
optimal growth in fed batch cultures,
(f) Selecting a monoclonal cell line from the cell clones of step (d) according to the screening criteria of step (e).

The invention further relates to a method for generating a host cell line characterized by the following steps
a) Providing a parental host cell, preferably a CHO or NSO cell,
b) Introducing a vector construct in said parental host cell of step (a) comprising a CERT S132A expression cassette,
c) Selecting for a stably transfected cell population,
d) Isolating monoclonal cell lines by FACS-based single-cell cloning,
e) Screening said monoclonal cell lines for
i) high levels of CERT S132A expression,
ii) optimal growth in seed stock cultures,
iii) optimal growth in fed batch cultures,
f) Selecting a monoclonal cell line from the cell clones of step (d) according to the screening criteria of step (e) as host cell line The invention furthermore relates to a method for generating a host cell characterized by the following steps
a) Providing a parental host cell, preferably a CHO or NSO cell,
b) Introducing a vector construct in said parental host cell of step (a) comprising a CERT S132A expression cassette,
c) Selecting for a stably transfected cell population,
d) Isolating cells by FACS-based single-cell cloning,
e) Screening said cells for
i) high levels of CERT S132A expression,
ii) optimal growth in seed stock cultures,
iii) optimal growth in fed batch cultures,
f) Selecting a single clone or a pool of cells according to the screening criteria of step (e) for the use as host cell.

Preferably said parental host cell of step (a) is a host cell as described above under s definitions. Preferably said parental host cell of step (a) is a rodent cell such as a mouse or hamster cell, most preferably a CHO DG44 cell.

Preferably said vector construct of step (b) comprises the following functional elements as depicted in FIG. 1B:
Cytomegalovirus (CMV) enhancer/promoter,
multiple cloning site (MCS),
CERT S132A expression cassette,
expression cassette encoding the puromycin N-acetyl transferase as selection marker in eukaryotic cells,
polyadenylation signal,
origin of replication,
beta-lactamase expression cassette for ampicillin resistance in bacteria.

Specific criteria for screening seed stock cultures in step (e) ii) for optimal growth are: viability, doubling time.

Specific criteria for screening fed batch cultures in step (e) iii) for optimal growth are: peak cell density, integral of viable cells over time (IVC), viability.

Said screening criteria in fed batch cultures are specifically significant, since they reflect the environmental conditions in an industrial production process.

In a preferred method the CERT S132A expression cassette of step (b) consists of SEQ ID NO:1.

The invention further relates to a method of producing a protein of interest encoded by a gene of interest in a cell as described above characterized by the following steps: a) Providing a cell as described above, b) Cultivating the cell, under conditions which allow the expression of at least one gene of interest. In a specific embodiment the method comprises the additional step of c) Harvesting the protein of interest. In an even more specific embodiment the method comprises another additional step of d) Purifying the protein of interest.

The invention furthermore relates to a method of producing a protein of interest encoded by a gene of interest in a cell as described above characterized by the following steps: a) Providing a cell as described above, b) Cultivating the cell, under conditions which allow the proliferation of the cell and expression of at least one gene of interest. In a specific embodiment the method comprises the additional step of c) Harvesting the protein of interest. In an even more specific embodiment the method comprises another additional step of d) Purifying the protein of interest.

The invention specifically relates to a method of producing a protein of interest encoded by a gene of interest in an inventive cell characterized by the following steps:
(a) Providing an inventive cell,
(b) Cultivating said cell, under conditions which allow the proliferation of the cell and expression of at least one gene of interest, (c) Harvesting the protein of interest and
(d) Purifying the protein of interest.

In a preferred production method the host cell comprises as selection and/or amplification marker for the gene of interest glutamine synthetase (GS) or DHFR, preferably DHFR.

The invention further relates to a method of identifying a cell which is transgene for CERT S132A (SEQ ID NO:1) by
(a) Performing a polymerase chain reaction PCR,
(b) Using genomic DNA as template, and
(c) Using the oligonucleotide primers with the SEQ ID NO: 2 and SEQ ID NO: 3,
whereby a 2373 bp PCR product is generated.

Optionally said cell is further characterized by a specific number of fragments and fragment sizes resulting from the incubation of the CERT-specific 2373 bp-PCR product with the following restriction enzymes:

| Enzyme | # Fragments | Fragment size (bps) |
| --- | --- | --- |
| EcoRV | 2 | 2236, 137 |
| HindIII | 2 | 2176, 197 |
| KpnI | 2 | 2142, 231 |
| NcoI | 2 | 2096, 277 |
| NdeI | 2 | 1973, 400 |
| PvuII | 2 | 1241, 1132 |
| SpeI | 2 | 2128, 245 |
| XhoI | 2 | 2257, 116 |
| AvaII | 3 | 1140, 832, 401 |
| BstXI | 3 | 1980, 266, 127 |
| SalI | 3 | 1673, 491, 209 |

The invention specifically relates to a method of identifying/characterizing a cell, which is transgene for CERT S132A (SEQ ID NO:1) by PCR using genomic DNA as template, whereby a 2373 bp PCR product is generated when using the oligonucleotide primers of SEQ ID NO: 2 and SEQ ID NO:3.

The invention further relates to a method of identifying/characterizing a cell, which is transgene for CERT S132A (SEQ ID NO:1) by PCR using genomic DNA as template, whereby a 2373 bp PCR product is generated when using the oligonucleotide primers of SEQ ID NO: 2 and SEQ ID NO:3 and whereby said cell is characterized by a specific number of fragments and fragment sizes resulting from the incubation of the CERT-specific 2373 bp-PCR product with the following restriction enzymes:

| Enzyme | # Fragments | Fragment size (bps) |
| --- | --- | --- |
| EcoRV | 2 | 2236, 137 |
| HindIII | 2 | 2176, 197 |
| KpnI | 2 | 2142, 231 |
| NcoI | 2 | 2096, 277 |
| NdeI | 2 | 1973, 400 |
| PvuII | 2 | 1241, 1132 |
| SpeI | 2 | 2128, 245 |
| XhoI | 2 | 2257, 116 |
| AvaII | 3 | 1140, 832, 401 |
| BstXI | 3 | 1980, 266, 127 |
| SalI | 3 | 1673, 491, 209 |

In a preferred embodiment of said method said cell is characterized by 2 specific fragments with the sizes according to the above table resulting from the incubation of the CERT-specific 2373 bp PCR product, which is generated using genomic DNA as template and the oligonucleotide primers of SEQ ID NO: 2 and SEQ ID NO:3, with the following restriction enzymes: EcoRV, KpnI, NcoI, NdeI, PvuII, SpeI, XhoI.

In a most preferred embodiment of said method said cell is characterized by 2 specific fragments with the sizes 2176 bp and 197 bp, respectively, resulting from the incubation of the CERT-specific 2373 bp PCR product, which is generated using genomic DNA as template and the oligonucleotide primers of SEQ ID NO: 2 and SEQ ID NO:3, with the restriction enzyme HindIII.

In a further embodiment the cell deposited with the DSMZ (Deutsche Sammlung von Mikroorganismen und Zellkulturen GmbH) under the number DSM ACC2989 (CHO/CERT 2.20) is characterized by a specific restriction digest or by a specific PCR band pattern, when using genomic DNA, whereby such assay generates a unique fingerprint specific for the genome integration site of the CERT transgene/the CERT S132A expression cassette in clone DSM ACC2989 (CHO/CERT 2.20). The cell line DSM ACC2989 (CHO/CERT 2.20) is uniquely described/characterized by junction fragments. The cell line DSM ACC2989 (CHO/CERT 2.20) is uniquely described/characterized by junction fragments between the inserted DNA (=the CERT transgene/the CERT S132A expression cassette) and the adjacent chromosomal DNA, whereby DNA (preferably genomic DNA) of the cell line is digested with one or more restriction enzymes such as EcoRV, HindIII, KpnI, NcoI, NdeI, PvuII, SpeI, XhoI, AvaII, BstXI, SalI and said junction fragments are identified, e.g by Southern blot analysis or PCR using one or more suitable optionally labelled DNA fragment(s). This DNA fragment(s) display(s) a specific band pattern or fingerprint characterizing the unique insertion site of the CERT transgene/the CERT S132A expression cassette in the genome of DSM ACC2989 (CHO/CERT 2.20).

In a further embodiment the cell deposited with the DSMZ (Deutsche Sammlung von Mikroorganismen und Zellkulturen GmbH) under the number DSM ACC2990 (CHO/CERT 2.41) is characterized by a specific restriction digest or by a specific PCR band pattern, when using genomic DNA, whereby such assay generates a unique fingerprint specific for the genome integration site of the CERT transgene/the CERT S132A expression cassette in clone DSM ACC2990 (CHO/CERT 2.41). The cell line is DSM ACC2990 (CHO/CERT 2.41) is uniquely described/characterized by junction fragments. The cell line DSM ACC2990 (CHO/CERT 2.41) is uniquely described/characterized by junction fragments between the inserted DNA (=the CERT transgene/the CERT S132A expression cassette) and the adjacent chromosomal DNA, whereby DNA (preferably genomic DNA) of the cell line is digested with one or more restriction enzymes such as EcoRV, HindIII, KpnI, NcoI, NdeI, PvuII, SpeI, XhoI, AvaII, BstXI, SalI and said junction fragments are identified, e.g by Southern blot analysis or PCR using one or more suitable optionally labelled DNA fragment(s). This DNA fragment(s) display(s) a specific band pattern or fingerprint characterizing the unique insertion site of the CERT transgene/the CERT S132A expression cassette in the genome of DSM ACC2990 (CHO/CERT 2.41).

The invention further relates to a method for cultivating a cell comprising a) providing a cell according to any one of claims 1 to 7 and b) cultivating said cell, under conditions which allow the proliferation of said cell. In a specific embodiment of said method, the cell additionally contains at least one (second/additional) vector construct comprising a gene of interest encoding a protein of interest. In a preferred embodiment said method comprises additionally harvesting the protein of interest. In another preferred embodiment said method further comprises purifying the protein of interest.

The invention furthermore relates to a use of the inventive cell (CHO/CERT 2.20=DSM ACC2989 or CHO/CERT 2.41=DSM ACC2990) for the manufacturing of proteins.

Furthermore, the invention relates to a reactor/fermentation vessel containing the inventive cell in a medium.

The invention also relates to a kit comprising an inventive cell, an expression vector for expression of a gene of interest and a cell culture medium for cultivation of said cell.

In a specific embodiment of the present invention said kit comprises an inventive cell, which additionally contains at least one (second) vector construct comprising a gene of interest encoding a protein of interest, whereby said cell is cultivated in a medium, which allows the proliferation of said cell in a reactor/fermentation vessel.

The invention furthermore relates to a cell comprising a CERT S132A expression cassette, wherein said cell is characterized by:
f) a specific PCR band pattern/fingerprint when using genomic DNA as template, whereby a 2373 bp PCR product is generated using the oligonucleotide primers of SEQ ID NO: 2 and SEQ ID NO:3 or
g) a specific PCR band pattern/fingerprint when using genomic DNA as template, whereby a 660 bp PCR product (SEQ ID NO: 6) is generated using the oligonucleotide primers of SEQ ID NO: 4 and SEQ ID NO: 5 or
h) a specific number of fragments and fragment sizes resulting from the incubation of the CERT-specific 2373 bp-PCR product of (a) with the following restriction enzymes:

| Enzyme | # Fragments | Fragment size (bps) |
|---|---|---|
| EcoRV | 2 | 2236, 137 |
| HindIII | 2 | 2176, 197 |
| KpnI | 2 | 2142, 231 |
| NcoI | 2 | 2096, 277 |
| NdeI | 2 | 1973, 400 |
| PvuII | 2 | 1241, 1132 |
| SpeI | 2 | 2128, 245 |
| XhoI | 2 | 2257, 116 |
| AvaII | 3 | 1140, 832, 401 |
| BstXI | 3 | 1980, 266, 127 |
| SalI | 3 | 1673, 491, 209 |

In a specific embodiment the CERT S132A expression cassette consists of the SEQ ID NO: 1. Preferably said cell is a CHO cell or a NS0 cell.

In a preferred embodiment said cell is deposited with the DSMZ (Deutsche Sammlung von Mikroorganismen und Zellkulturen GmbH) under the number DSM ACC2989 (CHO/CERT 2.20).

In a further preferred embodiment said cell is deposited with the DSMZ under the number DSM ACC2990 (CHO/CERT 2.41).

EXAMPLES

Materials and Methods
Cell Culture

All cell lines used at production and development scale are maintained in serial seedstock is cultures in surface-aerated T-flasks (Nunc, Denmark) in incubators (Thermo, Germany) or shake flasks (Nunc, Denmark) at a temperature of 37° C. and in an atmosphere containing 5% $CO_2$. Seedstock cultures are subcultivated every 2-3 days with seeding densities of 1-3E5 cells/mL. The cell concentration is determined in all cultures by using a hemocytometer. Viability is assessed by the trypan blue exclusion method.

Fed-Batch Cultivation

Cells are seeded at $3\times10^5$ cells/ml into 125 ml shake flasks in 30 ml of BI-proprietary production medium without antibiotics or MTX (Sigma-Aldrich, Germany). The cultures are agitated at 120 rpm in 37° C. and 5% $CO_2$ which is reduced to 2% following day 3. BI-proprietary feed solution is added daily and pH is adjusted to pH 7.0 using $NaCO_3$ as needed. Cell densities and viability are determined by trypan-blue exclusion using an automated CEDEX cell quantification system (Innovatis).

Detection of CERT S132A expression by intracellular FACS staining and Western blotting For intracellular staining, $1\times10^6$ cells are fixed in 1% paraformaldehyde in PBS for 20 min and permeabilized in PBS containing 0.05% Tween-20. Subsequently, cells are resuspended in 1% BSA/PBS and stained using an anti-Flag M2 monoclonal mouse antibody (Sigma) and an Alexa488-labeled goat anti-mouse antibody (Invitrogen). The fluorescent signal is quantitatively analysed by flow cytometry (FACScalibur, Coulter).

Whole cell extracts for Western blotting are prepared by lysis of $5\times10^6$ cells in NP40-buffer [1% (v/v) NP40, 50 mM HEPES pH 7.9, 150 mM NaCl, 1 mM EDTA, 5 mM EGTA, 25 mM NaF and 40 µL/mL Complete protease inhibitor solution (Roche)] for 15 min on ice. Lysates are cleared by centrifugation at 16,000×g for 10 min and the protein concentration in the samples is determined using a BCA1 assay kit (Sigma). For Western blot analysis, equal protein amounts are separated with MOPS buffer on NuPAGE 10% Bis-Tris gels (Invitrogen) according to the manufacturer's protocol. Protein is transferred onto PVDF membranes (Millipore) using transfer buffer in XCell II blot module (Invitrogen). After blocking for 1 h at room temperature with blocking agent (Invitrogen), membranes are probed with anti-Flag M2 antibody (Sigma). Proteins are visualised with peroxidase-coupled secondary antibody using the ECL Plus chemoluminescence detection system (Amersham Pharmacia).

Generation of Antibody-Producing Cells

CHO-DG44 cells as well as conCERT™ cell lines are stably transfected with expression plasmids encoding heavy and light chain of an IgG1-type antibody. By subsequent cultivation under selective conditions, stably transfected IgG producing cell populations are generated from both, the DG44 parental cell line and conCERT™ cells. The cell pools are further cultivated according to a standard stock culture regime with subcultivation every 2 to 3 days.

Determination of Recombinant Product Concentration by ELISA

To assess recombinant antibody production in IgG producer cells derived from CHO-DG44 cells and conCERT™ cell lines engineered to express the CERT S132A mutant, samples from cell supernatant are collected from standard inoculum cultures at the end of each passage for three consecutive passages. The product concentration is then analysed by enzyme linked immunosorbent assay (ELISA). The concentration of secreted monoclonal antibody product is measured using antibodies against human-Fc fragment (Jackson Immuno Research Laboratories) and human kappa light chain HRP conjugated (Sigma).

Single Cell Sorting

A 'FACS Vantage' (Becton Dickinson) flow cytometer equipped with pulse processing, sort enhancement module, and automatic cell deposition unit is used for analysis and cell sorting. On a dot plot of forward and side scatter (FSC/SSC) a gate is set around single living cells. Sorted cells are deposited into 96-well microtiter plates containing 200 µL growth medium at one cell per well with the automatic cell deposition unit.

Nucleic Acid Isolation and RT-PCR

Genomic DNA and total RNA from growing cells are isolated using TRIzol® reagent (Invitrogen, Germany) according to the manufacturer's instructions. The RNA is then treated with DNase I for 30 minutes at 37° C. First strand cDNA synthesis is carried out using the Cloned AMV First-Strand cDNA Synthesis Kit (Invitrogen, Germany) starting with 3 μg of total RNA and oligo(dT) oligonucleotides. Quantitative levels of the human CERT transcript are determined by real-time PCR using the Absolute™ QPCR SYBR® Green Fluorescein Mix (ABgene, Surrey, UK) and a thermal cycler controlled by the MyIQ Real Time Detection software (BioRad, Germany).

Unique amplificates for identification of conCERT™ cells are detected by PCR on genomic DNA using oligonucleotide primers:

```
CMV sense:
5' GACGTCAATGGGAGTTTGTTTTG 3'    (SEQ ID NO: 2)
and

Terminator anti-sense:
5' CAACTAGAAGGCACAGTCGAGG 3'.    (SEQ ID NO: 3)
```

Using either DNA or mRNA as template, CERT S132A expression is detected by RT-PCR using the oligonucleotide primers:

CERT-for: 5' GCGTTCTGATGGTGACTTCTTG 3' (SEQ ID NO: 4) and CERT-rev: 5' TGTCCTGTGACGCCTT-TAACTG 3' (SEQ ID NO: 5), resulting in a PCR product of 660 bp (SEQ ID NO: 6).

EXAMPLES

Generation & Characterization of Chopper® Cells

Example 1

Characterization and Unique Identification of CHO/CERT S132A Cell Lines

CHO/CERT S132A cell lines (which herein are also referred to as "conCERT™" cell is lines) can be described in general as cells with heterologous expression of the human CERT mutant S132A.

The CHO/CERT S132A cell lines described in the present invention contain a CERT expression cassette as depicted in FIG. 1A comprising: Upstream regulatory sequences 0.6 kb) derived from the CMV enhancer/promoter, Flag™ epitope tag preceding coding region of the human CERT gene (GeneID 10087) with a mutation changing serine 132 to alanine (SEQ ID NO: 1); TGA stop codon and 0.5 kb of 3' untranslated region including polyadenylation signal.

The vector construct used for generation of the CHO/CERT S132A cell lines described in the present invention is shown in FIG. 1B and contains the following functional elements:

Cytomegalovirus (CMV) enhancer/promoter
Expression cassette encoding the Flag™-tagged CERT-SA
Polyadenylation signal from bovine growth hormone (bGH pA)
Expression cassette for puromycin resistance
Origin of replication
Beta-lactamase expression cassette for Ampicillin-resistance in bacteria The two CHO/CERT S132A cell lines deposited with the DSMZ under the numbers DSM ACC2989 (CHO/CERT 2.20) and DSM ACC2990 (CHO/CERT 2.41) contain the CERT S132A expression construct stably integrated into their genomes.

CHO/CERT S132A cell lines containing this construct, such as the cell line deposited with the DSMZ under the number DSM ACC2989 (CHO/CERT 2.20) and the cell line deposited with the DSMZ under the number DSM ACC2990 (CHO/CERT 2.41), can be identified by PCR on genomic DNA. A specific set of oligonucleotide primers (SEQ ID NOs: 2 and 3) produces a distinct signal of 2373 bp size in this PCR reaction which allows to detect and thus identify CHO/CERT cells from cells which have not been transfected with the CERT S132A expression construct described above. Binding positions and orientation of the primers are depicted in FIG. 1B (arrow heads).

```
CMV sense:
5' GACGTCAATGGGAGTTTGTTTTG 3'    (SEQ ID NO: 2)

Terminator anti-sense:
5' CAACTAGAAGGCACAGTCGAGG 3'    (SEQ ID NO: 3)
```

When the 2373 PCR fragment is digested with restriction enzymes, a pattern of restriction fragments will result as summarized in TABLE 1.

TABLE 1

Restriction enzymes, number of fragments and fragment sizes resulting from the digestion of the CERT-specific 2373 bp-PCR product:

| Enzyme | # Fragments | Fragment size (bps) |
|---|---|---|
| EcoRV | 2 | 2236, 137 |
| HindIII (preferred) | 2 | 2176, 197 |
| KpnI | 2 | 2142, 231 |
| NcoI | 2 | 2096, 277 |
| NdeI | 2 | 1973, 400 |
| PvuII | 2 | 1241, 1132 |
| SpeI | 2 | 2128, 245 |
| XhoI | 2 | 2257, 116 |
| AvaII | 3 | 1140, 832, 401 |
| BstXI | 3 | 1980, 266, 127 |
| SalI | 3 | 1673, 491, 209 |

Using either DNA or mRNA as template, CERT S132A expression in conCERT cell lines can also be detected by PCR using the oligonucleotide primers: CERT-for: 5' GCGTTC-TGATGGTGACTTCTTG 3' (SEQ ID NO: 4) and CERT-rev: 5' TGTCCTGTGACGCCT-TTAACTG 3' (SEQ ID NO: 5), resulting in a PCR product of 660 bp with the following sequence (SEQ ID NO: 6):

```
GCGTTCTGATGGTGACTTCTTGCATAGTACCAACGGCAATAAAGAAAA

GTTATTTCCACATGTGACACCAAAAGGAATTAATGGTATAGACTTTAA

AGGGGAAGCGATAACTTTTAAAGCAACTACTGCTGGAATCCTTGCAAC

ACTTTCTCATTGTATTGAACTAATGGTTAAACGTGAGGACAGCTGGCA

GAAGAGACTGGATAAGGAAACTGAGAAGAAAAGAAGAACAGAGGAAGC

ATATAAAAATGCAATGACAGAACTTAAGAAAAAATCCCACTTTGGAGG

ACCAGATTATGAAGAAGGCCCTAACAGTCTGATTAATGAAGAAGAGTT

CTTTGATGCTGTTGAAGCTGCTCTTGACAGACAAGATAAAATAGAAGA

ACAGTCACAGAGTGAAAAGGTGAGATTACATTGGCCTACATCCTTGCC

CTCTGGAGATGCCTTTTCTTCTGTGGGGACACATAGATTTGTCCAAAA

GGTTGAAGAGATGGTGCAGAACCACATGACTTACTCATTACAGGATGT
```

```
AGGCGGAGATGCCAATTGGCAGTTGGTTGTAGAAGAAGGAGAAATGAA

GGTATACAGAAGAGAAGTAGAAGAAAATGGGATTGTTCTGGATCCTTT

AAAAGCTACCCATGCAGTTAAAGGCGTCACAGGACA.
```

The CERT S132A cell lines CHO/CERT S132A 2.20 and 2.41 that are described in the present invention can furthermore be identified by heterologous expression of the Flag-CERT-S132A fusion protein by Western Blot using antibodies raised either against the Flag™ epitope tag (e.g. anti-Flag M2 monoclonal mouse antibody (Sigma)) or the human CERT protein (e.g. CERT/GPBP antibody, clone BL2222, Bethyl Laboratories, Inc.). Both antibodies do not cross-react with the hamster CERT protein. Therefore, a CERT-specific signal will only be detected in CHO/CERT S132A cells, whereas this signal is absent in CHO cell lines which do not contain the CERT S132A expression construct.

The vector construct carrying the CERT expression cassette also contains a puromycin resistance gene. CHO/CERT S132A cells are therefore able to grow in the presence of 5-10 µg/ml puromycin in the culture medium.

The CHO/CERT S132A cell lines described in the present invention which are deposited with the DSMZ under the numbers DSM ACC2989 (CHO/CERT 2.20) and DSM ACC2990 (CHO/CERT 2.41) are derivatives of the CHO-DG44 cell line. Hence, they equally need the supplements hypoxanthine and thymidine in the cultivation medium for growth and survival (HT supplementation).

Example 2

Generation of Stably Transfected CHO/CERT S132A Cell Pools

Figure 1:
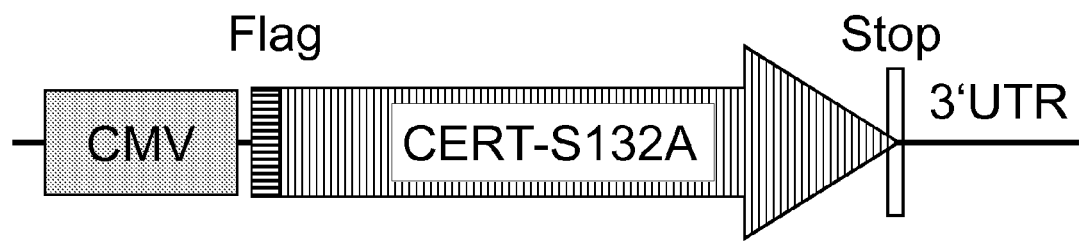
FIG. 1: SCHEMATIC REPRESENTATION OF THE CERT S132A EXPRESSION CONSTRUCT (A) Schematic representation of the Flag-CERT S132A expression cassette contained in the cell line deposited with the DSMZ under the number DSM ACC2989 (CHO/CERT 2.20) and the cell line deposited with the DSMZ under the number DSM ACC2990(CHO/CERT 2.41) cells. CMV=enhancer/promoter of the cytomegalovirus (CMV) early region; Flag=Flag™ epitope tag; CERT-S132A=cDNA of the human CERT S132A mutant; Stop=TGA stop codon; 3'UTR=3' untranslated region.
Figure 1:
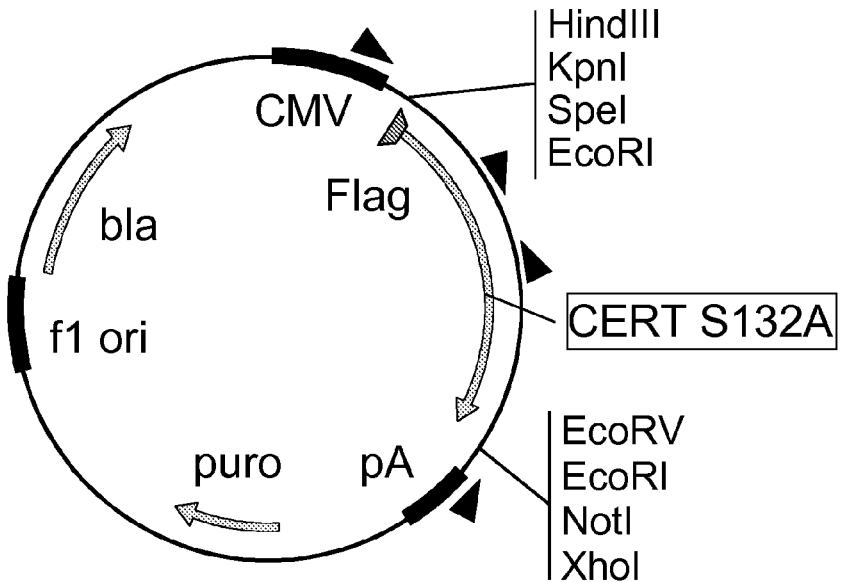

To generate the CHO/CERT S132A cell lines described in the present invention, CHO-DG44 cells [Urlaub et al., Cell 33, 1983] are transfected with an expression construct carrying an expression cassette for a mutant variant of the human CERT protein (CERT Ser132→Ala, herein referred to as "CERT-S132A"), fused to an N-terminal Flag™ epitope tag (FIG. 1).

The protein coding region has the following sequence (SEQ-ID NO: 1; sequence is given in 5'-3' orientation; start and stop codons are underlined and in bold print, Flag™-tag coding region is underlined and CERT coding region is represented in italics; mutated codon changing Ser132→Ala is marked by underlining and bold print):

```
GCCAGTGTGCTGGAATTCACCATGGCCCCACTAGCCGACTACAAGGAC

GACGATGACAAGATGTCGGATAATCAGAGCTGGAACTCGTCGGGCTCG

GAGGAGGATCCAGAGACGGAGTCTGGGCCGCCTGTGGAGCGCTGCGGG

GTCCTCAGTAAGTGGACAAACTACATTCATGGGTGGCAGGATCGTTGG

GTAGTTTTGAAAAATAATGCTCTGAGTTACTACAAATCTGAAGATGAA

ACAGAGTATGGCTGCAGAGGATCCATCTGTCTTAGCAAGGCTGTCATC

ACACCTCACGATTTTGATGAATGTCGATTTGATATTAGTGTAAATGAT

AGTGTTTGGTATCTTCGTGCTCAGGATCCAGATCATAGACAGCAATGG

ATAGATGCCATTGAACAGCACAAGACTGAATCTGGATATGGATCTGAA

TCCAGCTTGCGTCGACATGGGGCAATGGTGTCCCTGGTGTCTGGAGCA

AGTGGCTACTCTGCAACATCCACCTCTTCATTCAAGAAAGGCCACAGT

TTACGTGAGAAGTTGGCTGAAATGGAAACATTTAGAGACATCTTATGT

AGACAAGTTGACACGCTACAGAAGTACTTTGATGCCTGTGCTGATGCT

GTCTCTAAGGATGAACTTCAAAGGGATAAAGTGGTAGAAGATGATGAA

GATGACTTTCCTACAACGCGTTCTGATGGTGACTTCTTGCATAGTACC

AACGGCAATAAAGAAAAGTTATTTCCACATGTGACACCAAAAGGAATT

AATGGTATAGACTTTAAAGGGGAAGCGATAACTTTTAAAGCAACTACT

GCTGGAATCCTTGCAACACTTTCTCATTGTATTGAACTAATGGTTAAA

CGTGAGGACAGCTGGCAGAAGAGACTGGATAAGGAAACTGAGAAGAAA

AGAAGAACAGAGGAAGCATATAAAAATGCAATGACAGAACTTAAGAAA

AAATCCCACTTTGGAGGACCAGATTATGAAGAAGGCCCTAACAGTCTG

ATTAATGAAGAAGAGTTCTTTGATGCTGTTGAAGCTGCTCTTGACAGA

CAAGATAAAATAGAAGAACAGTCACAGAGTGAAAAGGTGAGATTACAT

TGGCCTACATCCTTGCCCTCTGGAGATGCCTTTTCTTCTGTGGGGACA

CATAGATTTGTCCAAAAGGTTGAAGAGATGGTGCAGAACCACATGACT

TACTCATTACAGGATGTAGGCGGAGATGCCAATTGGCAGTTGGTTGTA

GAAGAAGGAGAAATGAAGGTATACAGAAGAGAAGTAGAAGAAAATGGG

ATTGTTCTGGATCCTTTAAAAGCTACCCATGCAGTTAAAGGCGTCACA

GGACATGAAGTCTGCAATTATTTCTGGAATGTTGACGTTCGCAATGAC

TGGGAAACAACTATAGAAAACTTTCATGTGGTGGAAACATTAGCTGAT

AATGCAATCATCATTTATCAAACACACAAGAGGGTGTGGCCTGCTTCT

CAGCGAGACGTATTATATCTTTCTGTCATTCGAAAGATACCAGCCTTG

ACTGAAAATGACCCTGAAACTTGGATAGTTTGTAATTTTTCTGTGGAT

CATGACAGTGCTCCTCTAAACAACCGATGTGTCCGTGCCAAAATAAAT

GTTGCTATGATTTGTCAAACCTTGGTAAGCCCACCAGAGGGAAACCAG

GAAATTAGCAGGGACAACATTCTATGCAAGATTACATATGTAGCTAAT

GTGAACCCTGGAGGATGGGCACCAGCCTCAGTGTTAAGGGCAGTGGCA

AAGCGAGAGTATCCTAAATTTCTAAAACGTTTTACTTCTTACGTCCAA

GAAAAAACTGCAGGAAAGCCTATTTTGTTCTAGTATTAACAGGTACTA

GAAGATATGTTTTATCTTTTTTAACTTTATTTGACTAATATGACTG
```

Stably transfected cell pools are generated by selection in the presence of the antibiotic puromycin. Expression of the CERT-S132A transgene in the resulting stable cell pools is confirmed by Western blot using antibodies raised either against the Flag™ tag or the CERT-S132A protein itself.

Since the cellular productivity correlates with the CERT level, the cell pools with the highest CERT-S132A expression levels are selected for subsequent single-cell cloning.

Example 3

Generation and Screening of Monoclonal CHO/CERT S132A Cell Lines

Figure 3:
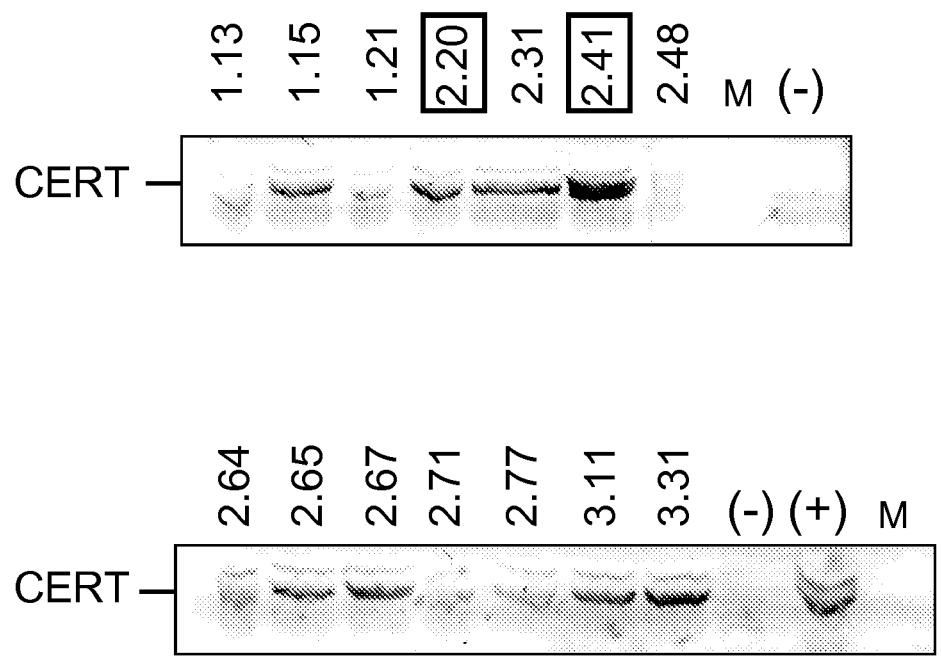

The stably transfected cell pools overexpressing CERT-S132A are subjected to FACS-based single cell cloning to generate monoclonal conCERT™ cell lines. The CHO/CERT S132A clones are then extensively screened with regards to two parameters: a) high level of CERT-S132A expression, b) optimal cell growth properties in both inoculum cultures and fed-batch processes. In a first round of selection, CERT-S132A expression is assessed in >100 CHO/CERT S132A clones by intracellular staining From these, the 15 clones with the highest level of intracellular CERT-S132A are selected for expansion and further analysis. CERT-S132A expression in the 15 selected CHO/CERT S132A clones is further assessed by Western Blot using anti-Flag™ antibodies (FIG. 3). Overexpression of the CERT-SA mutant is highest in the clones 1.15, 2.20, 2.31, 2.41, 2.65, 2.67, 3.11 and 3.31.

For an industrial production host cell line, good growth characteristics both in seed stock cultures as well as in fed-batch processes in serum-free chemically defined media are very important. Therefore, CHO/CERT S132A clones were cultivated according to standard industrial inoculum schemes and doubling time and viabilities were assessed. FIG. 4 shows the ranking of 15 CHO/CERT clones according to growth rate (A) and their viabilities over several culture passages (B). The two cell lines CHO/CERT S132A 2.20 (deposited at the DSMZ under the number DSM ACC2989) and CHO/CERT S132A 2.41 (deposited at the DSMZ under the number DSM ACC2990) are among the four clones with the highest doubling time and show a viability of 80-100% (FIG. 5A). Next, the growth of CHO/CERT S132A cell clones is investigated in a fed-batch fermentation in shake flasks which represents a small-scale model for biopharmaceutical production processes. As shown in FIG. 5A, all CHO/CERT S132A clones show the usual growth profile with an initial growth phase characterized by increasing cell concentrations which then reaches a plateau and subsequently decreases towards the end of the fermentation. However, the performance of the CHO/CERT S132A clones varies with regard to growth speed in the initial phase as well as the maximal cell densities. This translates into differences in the overall integral of viable cells (IVC) over the production process (FIG. 5B). From all analysed CHO/CERT S132A cell lines, clones 1.13, 2.20 and 2.41 show the highest IVCs which is even higher compared to the parental CHO-DG44 cell line (FIG. 5B). However, clone 1.13 has only low CERT-S132A expression and is therefore excluded. Therefore, the two cell lines described in the present invention CHO/CERT 2.20 (deposited at the DSMZ under the number DSM ACC2989) and CHO/CERT 2.41 (deposited at the DSMZ under the number DSM ACC2990) are selected as cells with high level of CERT-SA expression as well as excellent growth properties. Both cell lines are ideal candidates as optimized host cell lines for production of recombinant proteins.

Example 4

CHO/CERT S132A Cells as Host Cells for Recombinant Protein Production Using the GS System Cells deposited with the DSMZ under the numbers DSM ACC2989 (CHO/CERT 2.20) and DSM ACC2990 (CHO/CERT 2.41) are ideal host cells for recombinant protein production as they have an improved secretory capacity as well as good growth characteristics. As the parental DG44 cell line, they are dhfr-deficient and thus compatible with the most broadly used expression systems for recombinant proteins in the biopharmaceutical industry, namely the dihydrofolate reductase (DHFR). They are furthermore compatible with the glutamine synthetase (GS) selection/amplification systems as well as other commonly used selection strategies such as neomycin, bleomycin, hygromycin and zeozine.

Example 5

CHO/CERT S132A Cells as Host Cells for Recombinant IGG1 Antibody Production

To demonstrate their superior properties, the conCERT™ cells described in the present invention as well as the parental CHO-DG44 cell line are transfected with expression constructs encoding a human monoclonal IgG1-type antibody. Stably IgG-producing cell populations are generated by selection in serum-free chemically-defined medium without HT supplementation and in the presence of the antibiotic G418. Subsequently, they were subjected to gene amplification using methotrexate (MTX) as part as a standard industrial cell line development program. The resulting stable cell pools are than subjected to a fed-batch fermentation process in shake flasks. After 10 days, the cultures were harvested and the IgG concentration in the supernatant determined by ELISA. As shown in FIG. 6, the median harvest titers of the 10 highest producing pools derived from the parental CHO -DG44 cells are markedly lower compared to producer cells derived from the conCERT™ is cell lines. Furthermore, the 25-75% range of the DG44 antibody producer cells is below 400 mg/L, whereas it ranges from >400 up to nearly 1 g/L in CHO/CERT S132A IgG producer cells. Thus, the harvest titers obtained with producer cell pools from CHO/CERT S132A cells is about 2-fold higher compared to producer cell pools derived from the parental cell line.

These data demonstrate that the CHO/CERT S132A cells deposited with the DSMZ under the numbers DSM ACC2989 (CHO/CERT 2.20) and DSM ACC2990 (CHO/CERT 2.41) are superior host cells for recombinant protein production compared to the parental DG44 cell line.

Example 6

CHO/CERT S132A Cells as Host Cells for Recombinant Production of an IGG4 Antibody To demonstrate their superior properties, the conCERT™ cells described in the present invention as well as the parental CHO-DG44 cell line are transfected with expression constructs encoding a human monoclonal IgG4-type antibody. Stably IgG-producing cell populations are generated by selection in serum-free chemically-defined medium without HT supplementation and in the presence of the antibiotic G418. Subsequently, they were subjected to gene amplification using methotrexate (MTX) as part as a standard industrial cell line development program. The resulting stable cell pools are than subjected to a fed-batch fermentation process in shake flasks. After 10 days, the cultures were harvested and the IgG concentration in the supernatant determined by ELISA.

The median harvest titers of the 10 highest producing pools derived from the parental CHO-DG44 cells are markedly lower compared to producer cells derived from the conCERT™ cell lines. Furthermore, the 25-75% range of the DG44 antibody producer cells is below 400 mg/L, whereas it ranges from >400 up to nearly 1 g/L in CHO/CERT S132A IgG producer cells. Thus, the harvest titers obtained with producer cell pools from CHO/CERT S132A cells is about 2-fold higher compared to producer cell pools derived from the parental cell line.

Biopharmaceutical manufacturing requires the generation of monoclonal cell lines for use in cGMP production. Therefore, in the next step cell clones are generated from the highest expressing genetically heterogenous cell pools. The performance of the 10 highest expressing recombinant clones of each genotype are subsequently analysed in inoculum cultures as well as in fed-batch processes as described above. Also on the level of monoclonal cell lines, IgG4 producer clones originating from conCERT™ cell lines show significantly higher specific productivities (FIGS. 7A-10 highest expressing monoclonal cell lines from CHO/CERT 2.20 and 2.41 recombinant for IgG4-type antibody (conCERT™) compared to the 10 top clones derived from DG44 cells (classic)). Furthermore, this translates into higher overall IgG4 titres achieved with conCERT™ cells in fed-batch processes (FIG. 7B).

The example shows that the CHO/CERT S132A cells deposited with the DSMZ under the numbers DSM ACC2989 (CHO/CERT 2.20) and DSM ACC2990 (CHO/CERT 2.41) are superior host cells for recombinant protein production compared to the parental DG44 cell line.

Example 7

Increased Biopharmaceutical Protein Production of an FC Fusion-Protein From conCERT™ Cell Lines conCERT™ cells deposited with the DSMZ under the numbers DSM ACC2989 (CHO/CERT 2.20) and DSM ACC2990 (CHO/CERT 2.41) and CHO DG 44 cells are transfected with vectors encoding an Fc-fusion protein, meaning a therapeutically active (poly-)peptide covalently linked to the Fc-part of an IgG antibody, as the gene of interest. After selection, supernatant is taken from seed-stock cultures of all stable cell pools over a period of four subsequent passages, the product titer is determined by ELISA and divided by the mean number of cells to calculate the specific productivity. In comparison, product titers are markedly higher in producer cells generated from conCERT™ host cells compared to DG44 derived cells expressing the Fc-fusion protein.

Also in fed-batch cultures, conCERT™-derived cells have a significantly increased productivity of the fusion protein as well as higher titers at harvest.

This demonstrates, that use of conCERT™ host cells in cell line development enables the is generation of producer cell lines with enhanced specific production capacities as well as higher titres in serial cultures or in bioreactor batch or fed batch cultures.

Example 8 conCERT™ Cell Lines Represent Superior Host Cells for Biopharmaceutical Production of Single-Chain-FV (SCFV) Molecules and Domain Antibodies conCERT™ cells deposited with the DSMZ under the numbers DSM ACC2989 (CHO/CERT 2.20) and DSM ACC2990 (CHO/CERT 2.41) and CHO DG 44 cells are transfected with vectors encoding a single-chain-Fv (scFv) or a domain antibody (comprising one or more domains of the variable region of a single-chain antibody derived from lamas or other animals from the family of camelidae) as the gene of interest. After selection, supernatant is taken from seed-stock cultures of all stable cell pools over a period of four subsequent passages, the product titer is determined by ELISA and divided by the mean number of cells to calculate the specific productivity. In comparison, product titers are markedly higher in producer cells generated from conCERT™ host cells compared to DG44 derived cells expressing the scFv protein or the domain antibody.

Also in fed-batch cultures, conCERT™-derived cells have a significantly increased productivity of the fusion protein as well as higher titers at harvest.

This demonstrates, that use of conCERT™ host cells in cell line development enables the generation of producer cell lines with enhanced specific production capacities as well as higher titres in serial cultures or in bioreactor batch or fed batch cultures.

SEQUENCE TABLE:

| | |
|---|---|
| SEQ ID NO: 1 | Flag-CERT-SA coding region (2373 bp fragment generated using primers CMV sense (SEQ ID NO: 2) and Terminator anti-sense (SEQ ID NO: 3) |
| SEQ ID NO: 2 | Primer CMV sense |
| SEQ ID NO: 3 | Primer Terminator anti-sense |
| SEQ ID NO: 4 | Primer CERT-for |
| SEQ ID NO: 5 | Primer CERT-rev |
| SEQ ID NO: 6 | 660 bp PCR product obtained with primers CERT-for (SEQ ID NO: 4) and CERT-rev (SEQ ID NO: 5) |

REFERENCE LIST

Fallaux, F. J., Bout, A., van, d. V., I, van den Wollenberg, D. J., Hehir, K. M., Keegan, J., Auger, C., Cramer, S. J., van, O. H., van der Eb, A. J., Valerio, D., and Hoeben, R. C. (1998). New helper cells and matched early region 1-deleted adenovirus vectors prevent generation of replication-competent adenoviruses. Hum. Gene Ther. 9, 1909-1917.

Florin, L., Pegel, A., Becker, E., Hausser, A., Olayioye, M. A., and Kaufmann, H. Heterologous expression of the lipid transfer protein CERT increases therapeutic protein productivity of mammalian cells. Journal of Biotechnology *In Press, Corrected Proof*

Hanada, K., Kumagai, K., Yasuda, S., Miura, Y., Kawano, M., Fukasawa, M., and Nishijima, M. (2003). Molecular machinery for non-vesicular trafficking of ceramide. Nature 426, 803-809.

Urlaub, G., Kas, E., Carothers, A. M., and Chasin, L. A. (1983). Deletion of the diploid dihydrofolate reductase locus from cultured mammalian cells. Cell 33, 405-412.

The invention claimed is:

1. A cell deposited with the DSMZ (Deutsche Sammlung von Mikroorganismen und Zellkulturen GmbH) under the accession number DSM ACC2989 (CHO/CERT 2.20) or under the accession number DSM ACC2990 (CHO/CERT 2.41).

2. The cell according to claim 1, wherein said cell is deposited with the DSMZ under the accession number DSM ACC2990 (CHO/CERT 2.41).

3. The cell according to claim 1, wherein said cell deposited is with the DSMZ under the accession number DSM ACC2989 (CHO/CERT 2.20).

4. A kit comprising the cell according to claim 1, an expression vector for expression of a gene of interest and a cell culture medium for cultivation of said cell.

5. The cell according to claim 1, wherein the cell further comprises at least one second vector construct comprising a gene of interest operatively linked to a regulatory sequence, wherein the gene of interest encodes a protein of interest.

6. The cell according to claim 5, wherein said at least one second vector construct is stably integrated into the cells genome.

7. The cell according to claim 5, wherein the protein of interest is a therapeutic protein.

8. The cell according to claim 7, wherein the protein of interest is an antibody or an antibody fusion protein.

9. A method of producing a protein of interest encoded by the gene of interest in a cell of claim 5, wherein said method comprises the following steps:
   a) providing the cell according to claim 5,
   b) cultivating the cell, under conditions which allow the expression of the gene of interest.

10. The method of claim 9, wherein the method comprises the additional step of
    c) harvesting the protein of interest.

11. The method of claim 10, wherein the method comprises the additional step of
    d) purifying the protein of interest.

12. A method for cultivating the cell of claim 1, the method comprising
    a) providing the cell and
    b) cultivating said cell, under conditions which allow the proliferation of said cell.

* * * * *